(12) United States Patent
Goméz et al.

(10) Patent No.: US 11,116,184 B2
(45) Date of Patent: Sep. 14, 2021

(54) AUTOMATED NONINVASIVE DETERMINING THE FERTILITY OF A BIRD'S EGG

(71) Applicant: TECHNISCHE UNIVERSITÄT MÜNCHEN, Munich (DE)

(72) Inventors: Pedro A. Goméz, Munich (DE); Miguel Molina-Romero, Munich (DE); Axel Haase, Rimpar (DE); Benjamin Schusser, Freising (DE); Maximilian Aigner, Velden (DE); Maria Laparidou, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 16/760,735

(22) PCT Filed: Nov. 13, 2018

(86) PCT No.: PCT/EP2018/081030
§ 371 (c)(1),
(2) Date: Apr. 30, 2020

(87) PCT Pub. No.: WO2019/092267
PCT Pub. Date: May 16, 2019

(65) Prior Publication Data
US 2020/0348248 A1    Nov. 5, 2020

(30) Foreign Application Priority Data

Nov. 13, 2017 (EP) ..................... 17201373
Dec. 22, 2017 (EP) ..................... 17210164

(51) Int. Cl.
*G01N 24/08*  (2006.01)
*G01N 33/08*  (2006.01)
(Continued)

(52) U.S. Cl.
CPC .............. *A01K 43/04* (2013.01); *B07C 5/344* (2013.01); *G01N 24/085* (2013.01); *G01N 33/08* (2013.01);
(Continued)

(58) Field of Classification Search
CPC .. A01K 43/04; G01R 33/307; G01R 33/5611; G01R 33/3415; G01R 33/5608;
(Continued)

(56) References Cited

U.S. PATENT DOCUMENTS 6,029,080 A    2/2000   Reynnells et al.
6,149,956 A    11/2000  Boerjan
(Continued)

FOREIGN PATENT DOCUMENTS

EP    0890838 A1    1/1999
RU    2 436 296 C2  3/2010
(Continued)

OTHER PUBLICATIONS

Tanno, Ryutaro, et al. "Bayesian image quality transfer with CNNs: exploring uncertainty in dMRI super-resolution." International Conference on Medical Image Computing and Computer-Assisted Intervention. Springer, Cham, May 2017. (Year: 2017).*
(Continued)

*Primary Examiner* — Rishi R Patel
(74) *Attorney, Agent, or Firm* — Sunstein LLP

(57) ABSTRACT

Shown herein is a method of automated noninvasive determining the fertility of a bird's egg (14), comprising the following steps: conveying a plurality of bird eggs (14) sequentially or in parallel into an NMR apparatus (18), subjecting the bird eggs (14) to an NMR measurement, such as to generate a $_3$-D NMR image of at least a part of each of said eggs (14), said $_3$-D NMR image having a spatial resolution in at least one dimension of 1.0 mm or less,
(Continued)

preferably of 0.50 mm or less, wherein said part of the egg (14) includes the germinal disc of the respective egg (14), determining a prediction of the fertility according to at least one of the following two procedures: (i) deriving at least one feature from each of said $_3$-D NMR images, and employing said at least one feature in a feature-based classifier for determining a prediction of the fertility, and (ii) using a deep learning algorithm, and in particular a deep learning algorithm based on convolutional neural networks, generative adversarial networks, recurrent neural networks or long short-term memory networks.

20 Claims, 9 Drawing Sheets

(51) Int. Cl.
| | |
|---|---|
| *G01R 33/561* | (2006.01) |
| *G01R 33/56* | (2006.01) |
| *G01R 33/30* | (2006.01) |
| *B07C 5/344* | (2006.01) |
| *A01K 43/04* | (2006.01) |
| *G01R 33/3415* | (2006.01) |

(52) U.S. Cl.
CPC ....... *G01R 33/307* (2013.01); *G01R 33/3415* (2013.01); *G01R 33/561* (2013.01); *G01R 33/5608* (2013.01); *G01R 33/5611* (2013.01)

(58) Field of Classification Search
CPC ............. G01R 33/561; G01R 33/4835; G01R 33/483; B07C 5/344; G01N 24/085; G01N 33/08
See application file for complete search history.

(56) References Cited

U.S. PATENT DOCUMENTS

| | | | |
|---|---|---|---|
| 8,486,690 | B2 | 7/2013 | Burns |
| 9,835,560 | B2 | 12/2017 | Galli et al. |
| 10,852,284 | B2 | 12/2020 | Steiner et al. |
| 2006/0279281 | A1 | 12/2006 | Rapoport |
| 2009/0165723 | A1 | 7/2009 | Moran |
| 2015/0260704 | A1 | 9/2015 | Bruins et al. |
| 2016/0057977 | A1 | 3/2016 | Sewiolo et al. |
| 2018/0292335 | A1* | 10/2018 | Patman ................ G01R 33/448 |
| 2019/0128980 | A1* | 5/2019 | Porter ................ G01R 33/5611 |
| 2019/0383782 | A1 | 12/2019 | Steiner et al. |

FOREIGN PATENT DOCUMENTS

| | | |
|---|---|---|
| RU | 2008 137 794 A | 3/2010 |
| RU | 2 612 370 C1 | 3/2017 |

OTHER PUBLICATIONS

International Searching Authority/European Patent Office, International Search Report and Written Opinion of the International Searching Authority, Application No. PCT/EP2018/081030, dated Feb. 12, 2019, 17 pages.
A. Davenel et al., *Attempts for early gender determination of chick embryos in ovo using Magnetic Resonance Imaging*, Jun. 1, 2005, http://www.wpsa.com/index.php/publications/wpsa-proceedings/2015/xxii-european-sympo sium-on-the-quality-of-poultry-meat-and-the-xvi-european-symposium-on-the-quality-of-eggs-and-egg-products/2196-attempts-for-early-gender-determination-of-chick-embryos-in-ovo-using-magnetic-resonance-imaging/file [retrieved on Mar. 23, 2018] 4 pages.
S. Klein et al., *Localization of the fertilized germinal disc in the chicken egg before incubation*, Poultry Science, vol. 81, No. 4, Apr. 1, 2002, pp. 529-536 XP055461661.

* cited by examiner

AUTOMATED NONINVASIVE DETERMINING THE FERTILITY OF A BIRD'S EGG

CROSS-REFERENCE TO RELATED APPLICATIONS

This application is the national phase entry of International Patent Application No. PCT/EP2018/081030 filed on Nov. 13, 2018, and claims the benefit of EP Patent Application No. 17201373.2 filed Nov. 13, 2017 and EP Patent Application No. 17210164.4 filed Dec. 22, 2017, the disclosures of which are incorporated herein by reference in their entirety.

FIELD OF THE INVENTION

The present invention is in the field of egg production. More particularly, the present invention relates to a method of and an apparatus for noninvasive determining the fertility of a bird's egg, in particular a chicken egg.

BACKGROUND OF THE INVENTION

In the poultry industry it is desired to noninvasively determine the fertility of an egg. The poultry industry is one of the most important sources of animal protein for human consumption. The magazine *Poultry Trends* 2016 estimates that the worldwide production and consumption of poultry meat will increase by 20% by 2025, to over 130 million metric tons. In 2016, the global market already produced 116.4 million metric tons of poultry meat, where the top 185 poultry producing companies slaughtered close to 38 billion heads to satisfy global demand. In the United States alone, the poultry industry was valued at $38.7 billion USD.

Despite its significant volume, the process of incubating eggs to hatch poultry is far from perfect. An average poultry facility only hatches 75%-85% of the eggs it incubates. The other 15-25% of eggs either undergo early embryonic death or are not fertile. Currently, infertile and dead embryos are separated from live embryos after 18 days of incubation with noninvasive technologies, such as the Embrex® Egg remover (embrexbiodevices.com). While this solution prevents the unnecessary opening of eggs, it is still wasteful: all of the eggs with no chick inside are disposed of That is, the industry incubates more than 12.8 billion eggs annually only to throw them away. Hence, a solution that could determine the fertility status of an egg before incubation would be highly desired. Such a solution would dramatically increase productivity and save energy, costs and waste. Also, it would incorporate billions of eggs into the market for human consumption.

There are several patents in the field of identifying fertile eggs. For example, U.S. Pat. No. 5,745,228—Method and apparatus for distinguishing live from infertile poultry eggs uses a light source to determine if the poultry inside the egg is alive. This is the technology used in the Embrex® Egg remover.

U.S. Pat. No. 6,029,080—Method and apparatus for avian pre-hatch sex determination proposes the use of MRI for sexing members of avian species of an egg. While this patent uses MRI technology, it makes no reference to the determination of the fertility status and focuses exclusively on identifying the gonads via MRI for sexing.

U.S. Pat. No. 7,950,439 B1—Avian egg fertility and gender detection suggests the use of an external light source in the form of incandescent, fluorescent or LED lights for the determination of both fertility and gender of an avian egg.

U.S. Pat. No. 6,535,277 B2—Methods and apparatus for non-invasively identifying conditions of eggs via multi-wavelength spectral comparison relies on the use of visible and invisible light at wavelengths between 300 nm and 1,100 nm to identify multiple conditions of an egg, including the fertility status.

US2013/0044210 AI—Hyperspectral identification of egg fertility and gender uses light at the mid-IR to determine the fertility of an egg. The inventors of this patent claim that they are capable of determining the fertility status of an egg on day zero (i.e. freshly laid) with an accuracy of 90%.

EP 0 890 838 B1 discloses a method and an apparatus for selecting eggs according to their fertility. According to this method, eggs are subjected to nuclear magnetic resonance (NMR) treatment for obtaining an NMR image, and eggs are selected from a plurality of eggs according to a particular characteristic, on the basis of the NMR image. According to one embodiment, with the NMR image, the proton configuration in the yolk is determined. The inventors claim that the fertilization of an egg leads to a specific change of the proton configuration, especially in the yolk of the egg in question, which would be observable through an NMR treatment, even directly after laying. It is therefore argued that the fertility of the egg could be determined based on the proton configuration. In another embodiment, it is suggested to determine, with the aid of the NMR image, whether cell division in the egg, in particular in the germinal disc, has occurred as a result of fertilization. Neither a specific example or NMR images are shown for this variant, nor it is described how the distinction should be made. The application only mentions that the NMR image should be "compared with NMR images stored in a database". In fact, it is not even clear whether the inventors of this prior art patent truly did mean to analyze or ever have analyzed the germinal disc properly. Namely, while this application refers to the "so-called latebra on which lies the germinal disc in the center of the yolk", it is to be noted that the germinal disc does not lie on the latebra and is not located in the center of the yolk, but in an outside portion of the yolk and is only connected with the latebra via a long neck. At any rate, to the knowledge of the inventors, egg fertility determination methods and apparatuses based on NMR imaging have not been able to operate in a sufficiently reliable and efficient manner such as to find practical use so far.

SUMMARY OF THE INVENTION

The problem underlying the invention is to provide a non-invasive technique that is capable of automatically identifying infertile eggs immediately after laying and before incubation, and that is able to handle a large throughput of eggs and does not damage or alter the eggs in any form. This object is achieved by means of a method according to claim 1 and an apparatus according to claim 20. Preferable embodiments are defined in the dependent claims.

According to the present invention, a method of automated noninvasive determining the fertility of a bird's egg is provided, which comprises the following steps:

conveying a plurality of bird eggs sequentially or in parallel into an NMR apparatus, subjecting the bird eggs to an NMR measurement, such as to generate a 3-D NMR image of at least a part of each of said eggs, said 3-D NMR image having a spatial resolution in at least one dimension of 1.0 mm or less, preferably of 0.50 mm or less, wherein said part of the egg includes the germinal disc of the respective egg, determining a prediction of the fertility according to at least one of the following two procedures:

(i) deriving at least one feature from each of said 3-D NMR images, and employing said at least one feature in a feature-based classifier for determining a prediction of the fertility, wherein said at least one feature is chosen from the group consisting of a diameter of the germinal disc, the volume of the germinal disc, the shape of the germinal disc, the texture of the germinal disc, the location of the germinal disc in the egg, the texture of the yolk, a number and/or position of NMR-visible rings in the yolk, a contrast of the rings within the yolk, a texture, a volume or a shape of the latebra, the length of the neck of the latebra and ratios between the volumes or surfaces of two or more of the yolk, the latebra, the germinal disc and the albumen, and (ii) using a deep learning algorithm, and in particular a deep learning algorithm based on convolutional neural networks, generative adversarial networks, recurrent neural networks or long short-term memory networks.

The inventors have found out that the fertility of a chicken egg can be discerned from 3-D NMR images including the germinal disc thereof. Since the eggs can be subjected to NMR measurements without causing any harm or damage to the shell or to the interior, the hatching rate is not adversely affected by this measurement. At the same time, unnecessary incubation of infertile eggs can be avoided. Moreover, since the infertility is determined prior to incubation, those eggs found to be infertile can still be used for eating, which is not possible once incubation has started.

More precisely, when processing the image such as to determine for example the diameter of the germinal disc or the volume of the germinal disc, it is seen that both, the diameter and the volume differ consistently between fertile and infertile eggs such that these features can be used to distinguish between them. However, for a reliable distinction, according to the invention, a machine-based learning procedure is used.

According to one variant of the invention, at least one, but preferably at least two features are derived from the 3-D NMR image, and the feature(s) is/are used in a feature-based classifier for determining the fertility. Herein, the expression "deriving a feature from a 3-D NMR image" has a broad meaning, and shall encompass any possible manner by which the feature can be obtained based on the data representing a 3-D image. For example, the raw image data may be passed through a suitable filter that is designed to extract the feature in question from the data. However, other types of image processing or image data processing for deriving features would likewise be possible.

In the present disclosure, the features to be extracted from the 3-D NMR image are predetermined or "hand-crafted". Importantly, at least one, preferably at least two of these features are used in the feature-based classifier. A particularly advantageous choice for at least one feature is the volume, the diameter or a feature related to the shape or the texture of the germinal disc. However, other features are likewise indicative of the fertility of the egg and can be used as one of the at least one feature(s) in the feature-based classifier, for example the location of the germinal disc in the egg, the texture of the yolk, a number and/or position of NMR-visible rings in the yolk or a contrast of the rings within the yolk. "NMR-visible rings" relate to ring-like structures that can be seen in the NMR-image of the yolk and will be shown below. Further features that can be employed are a texture, a volume or a shape of the latebra, the length of the neck of the latebra or ratios between the volumes or surfaces of two or more of the yolk, the latebra, the germinal disc and the albumen. If two or more features are employed in the feature-based classifier, at least one of them is selected from the above-mentioned features. In particularly preferred embodiments, at least one of the two or more features is selected from the group consisting of the diameter, volume or shape of the germinal disc. Moreover, the procedure (i) is preferably a machine learning-based procedure.

Moreover, if the NMR image is constituted by voxels, the "spatial resolution in one dimension" referred to above is the size of a voxel in the corresponding dimension. Preferably, the spatial resolution in at least two, more preferably in all three dimensions is 1.0 mm or less, preferably 0.5 mm or less.

Instead of basing the analysis on predetermined or "hand-crafted" features, in an alternative variant, the prediction of the fertility is carried out using a deep learning algorithm, and in particular a deep learning algorithm based on convolutional neural networks, generative adversarial networks, recurrent neural networks or long short-term memory networks. In other words, rather than telling the algorithm what features should be considered for the purpose of classification regarding fertility, using the second variant, the algorithm itself finds the characteristic features by a learning process. Indeed, the inventors could show that using a convolutional neural network algorithm on the 3-D NMR images, the fertility state of the egg could be predicted with a precision of 97.3% with reasonable training.

In a preferred embodiment, the step of determining the prediction of the fertility is carried out by a classification module, wherein said method further comprises a step of conveying said plurality of bird eggs out of said NMR apparatus and sorting the eggs according to the fertility prediction provided by said classification module.

In a preferred embodiment, the feature-based classifier employs a kernel method, in particular a support vector machine, a relevance vector machine or a kernel perceptron, a quadratic discriminant analysis or a linear discriminant analysis, classification trees, random forests or a naïve Bayes classifier.

"Kernel methods" as used herein are understood as methods that make use of kernel functions that allow working in a high-dimensional space where features can be rearranged for an easier identification of patterns and class borders. A suitable kernel method for the purposes of the invention is a support vector machine (SVM). Given a set of training features, SVMs find a linear representation that separates the classes with the widest possible margin. When a new data point is to be classified, SVMs place it in one of the groups in a non-probabilistic fashion. It is at its core a linear classifier, but it can solve non-linear problems by finding the right kernel function. For further details on support vector machines, reference is made to Cristianini, N. & Shawe-Taylor, J. *An Introduction to Support Vector Machines and other kernel based learning methods. Ai Magazine* 22, 190 (2000).

A further preferable kernel method for the purpose of the present invention is the relevance vector machine (RVM). It is in essence a SVM using a probabilistic kernel (typically Gaussian) to yield a probabilistic classification. For additional details on relevance vector machines, reference is made to Tipping, M. E. *Sparse Bayesian Learning and the Relevance Vector Machine. J. Mach. Learn. Res.* 1, 211-244 (2001).

Another advantageous method is the kernel perceptron. While the models learnt by the classical perceptron are only applicable to linear binary classification problems, the kernel perceptron operates in a high dimensional space where the proper kernel function can transform a non-linear problem into a linear one (see also Dekel, O., Shalev-Shwartz, S. & Singer, Y. *The forgetron: a kernel-based perceptron on a budget. SLAM J. Comput.* 37/5, 1342-1372 (2008).

The linear discriminant analysis (LDA) is a method which tries to identify a linear combination of features that separates two or more classes. Thus, during training it assumes Gaussian distributions of the conditional probability density functions of each class and learns a classification threshold that depends on the mean and covariance of these distributions. For further details, reference is made to Mika, S., Ratsch, G., Weston, J., Schulköpf, B. & Muller, K.-R. *Fisher discriminant analysis with kernels. Ieee* 41-48 (1999). doi: 10.1109/NNSP.1999.788121, and McLachlan, G. J. *Discriminant analysis and statistical pattern recognition. Wiley series in probability and statistics* (2004). doi:10.1002/0471725293. LDA is a simplification of quadratic discriminant analysis (QDA), where one assumes homoseedasticity, meaning that the covariance of conditional probability density functions of each class are equal. If that is the case, the quadratic term of QDA can be dismissed from the formal equation. At their core LDA and QDA share the same concept and formulation: one uses the probabilistic information that can be derived from the features to find the linear (LDA) or quadratic (QDA) threshold that best separates the classes.

Classification trees are tree structures which accept feature vectors as input in the trunk of the tree, leafs represent class labels and branches the conjunctions of features that lead the path through the tree. During training, the decision threshold of each branch in the features' space is learnt. They have however been found to be prone to overfitting. For further details, reference is made to Rokach, L. & Maimon, O. *Data mining with decision trees: Theory and applications. World Scientific Pub Co Inc* (2008).

A random forest as understood herein is an ensemble of randomly grown classification trees. The working principle is based on averaging the output of multiple classification trees to reduce overfitting. For further details, reference is made to Breiman, L. *Random forests. Mach. Learn.* 45, 5-32 (2001).

Naïve Bayes classifiers are a family of probabilistic classifiers. They are based on the Bayes' theorem and assume independence of the features (hence termed naïve). Classification is based on the maximum a posteriori criterion, that is, finding the class for which the product of its likelihood and a priory probability is maximum. Likelihood and a priory probability are learnt from the training data. For further details, reference is made to Rish, I. *An empirical study of the naive Bayes classifier. Empir. methods Artif. Intell. Work. IJCAI* 22230, 41-46 (2001).

In a preferred embodiment, the method comprises applying a boosting technique, in particular an adaptive boosting technique, a logistic boosting technique or a probabilistic boosting-tree technique.

"Boosting techniques" as understood herein are techniques that create aggregations of "weak" classifiers to build a "strong" classifier. A "weak" classifier is defined as any classification method that performs slightly better than random guessing, while "strong" classifiers are well-correlated with the true classification. In this sense, a random forest can also be seen as a boosting technique. For the purposes of the present invention, three preferred methods are:

Adaptive boosting (AdaBoost): The output of the weak classifiers is combined in a weighted sum. Unlike neural networks or SVMs, AdaBoost selects during training only those features that improve the classification power of the model (cf. Freund, Y. & Schapire, R. E. *A Decision-Theoretic Generalization of On-Line Learning and an Application to Boosting. J. Comput. Syst. Sci.* 55, 119-139 (1997)).

Logistic boosting (LogitBoost): Evolution of AdaBoost into a probabilistic formulation. For a detailed description, see reference is made to Jerome Friedman, Trevor Hastie and Robert Tibshirani. *Additive logistic regression: a statistical view of boosting. Annals of Statistics* 28 (2), 2000.337-407.

Probabilistic boosting tree: This automatically builds a tree in which each node combines a number of weak classifiers into a strong classifier (cf. Tu, Z. *Probabilistic boosting-tree: Learning discriminative models for classification, recognition, and clustering. in Proceedings of the IEEE International Conference on Computer Vision II,* 1589-1596 (2005)).

In a preferred embodiment, in said NMR measurement, a histogram of diffusion coefficients in various locations in the egg is further determined, and wherein said prediction of the fertility is further based on the shape of the histogram.

The inventors have found that the shape of a histogram of diffusion coefficients in various locations in the egg differs for fertile and infertile eggs. Herein, the histogram indicates how frequent certain diffusion coefficients occur when measurements at various locations in the egg are made. Accordingly, by analyzing the shape of the diffusion coefficient histogram, the fertility can be predicted. The prediction based on the shape of the diffusion coefficient histogram can then be used to augment a prediction based on the above referenced methods.

While there are of course many ways to analyze the shape of a diffusion coefficient histogram, in a preferred embodiment, determining the fertility based on the shape of the histogram of diffusion coefficients comprises comparing the frequency of occurrence of at least two different diffusion coefficients or diffusion coefficient ranges. This is a particularly simple way to characterize the shape of the diffusion coefficient histogram, which has proven to give surprisingly reliable results.

In a preferred embodiment, said at least two different diffusion coefficients, or the centers of said at least two diffusion coefficient ranges are separated by between 0.5 and 2.5 $mm^2/s$, more preferably by between 0.75 and 1.5 $mm^2/s$.

Of said at least two different diffusion coefficients, or of the centers of said at least two diffusion coefficient ranges, one is preferably located in a range of 0.6 to 1.3 $mm^2/s$, more preferably in a range of 0.7 to 1.2 $mm^2/s$, and the other one is preferably located in a range of 1.5 to 2.5 $mm^2/s$, more preferably in a range of 1.7 to 2.3 $mm^2/s$.

In a preferred embodiment, said various locations in the egg are evenly distributed in the egg, and in particular, correspond to voxels of a diffusion coefficient image.

In a preferred embodiment, in said NMR measurement, an NMR spectrum of the yolk including peaks corresponding to water and fat is obtained, and the prediction of the fertility is further based on said NMR spectrum.

The inventors have found that equally surprisingly, the NMR spectra of the yolk of fertile and infertile eggs differ with regard to their peaks corresponding to water and fat. Accordingly, the shape of an NMR spectrum including such water and fat peaks is likewise characteristic for the fertility and can be employed in the determination.

Having regard to the spectrum, the inventors have observed that when the spectrum is e.g. normalized to the peaks corresponding to fat, the peak corresponding to water is larger in an infertile egg as compared to a fertile egg. Accordingly, one way to determine the fertility is via the ratio of the water and fat peaks. However, there are different ways of classifying fertility based on the NMR spectra. In particular, it is possible to present the spectrum, or certain characteristics of the spectrum, such as peak heights and peak locations to a machine learning module which carries out the classification.

The fertility prediction based on the NMR spectra can then be used to further augment the prediction based on the methods described above.

In a preferred embodiment, the eggs are arranged in a regular pattern, in particular in a matrix configuration, on a tray during said conveying and NMR measurement. Preferably, the number of eggs arranged on said tray is at least 36, more preferably at least 50 and most preferably at least 120.

In a preferred embodiment, said NMR apparatus comprises an array of RF coils for applying RF magnetic fields to the eggs located on the tray and/or for detecting NMR signals, said array of RF coils comprising one or more of
- a plurality of coils arranged in a plane located above the tray loaded with eggs when conveyed to the NMR apparatus,
- a plurality of coils arranged in a plane located underneath the tray loaded with eggs when conveyed to the NMR apparatus,
- a plurality of coils arranged in vertical planes extending between rows of eggs on the tray when conveyed to the NMR apparatus, which rows extend in parallel with the conveying direction of the tray into and out of the NMR apparatus.

In case of the plurality of coils arranged in a plane located above or underneath the tray loaded with eggs, the ratio of the number of coils to the number of eggs arranged on said tray is preferably between 1:1 to 1:25, more preferably between 1:1 to 1:16, and most preferably between 1:1 to 1:5.

In a preferred embodiment, said NMR apparatus comprises an array of RF coils for applying RF magnetic fields to the eggs located on the tray (16) and/or for detecting NMR signals, said array of RF coils being integrated with or attached to said tray.

Herein, the tray preferably comprises a plurality of dimples or pockets for receiving a corresponding egg, wherein a number of coils is associated with each of said dimples or pockets, wherein said number of coils per dimple or pocket is at least 1, preferably at least 2, more preferably at least 3 and most preferably at least 4, and/or wherein at least some of said coils are arranged vertically with respect to the main plane of the tray, or with an angle of at least 50°, preferably of at least 75 and most preferably of at least 80° with respect to the main plane of the tray.

In a preferred embodiment, said 3-D NMR images of the plurality of eggs are obtained using parallel imaging, in which coherent images from an array of eggs based on measurements with multiple RF coils are reconstructed.

In a preferred embodiment, said 3-D NMR images of the plurality of eggs are obtained using a simultaneous multi-slice (SMS) technique, in which multiplexed images from an array of eggs based on measurements at different frequency bands are reconstructed.

In a preferred embodiment the 3-D NMR images are generated using compressed sensing, permitting to recover images from measurements sampled below the Nyquist frequency.

In a preferred embodiment, the 3-D NMR images are generated using steady-state free precession, fast low-angle shot imaging and/or quantitative transient-state imaging.

In a preferred embodiment, the method further comprises a step of improving the quality of the NMR image by means of a quality transfer technique.

Preferably, the number of eggs conveyed in parallel to said NMR apparatus and the generation of NMR images is adapted such that the determining of the fertility prediction is carried out at a rate of 20 seconds per egg or less, preferably of 10 seconds per egg or less, and most preferably of 2 seconds per egg or less.

In a preferred embodiment, a 3-D NMR image of a plurality of eggs arranged in a regular pattern, in particular in a matrix configuration, is generated, and the image is divided into images corresponding to the individual eggs, which are subjected to said fertility prediction determining.

In a preferred embodiment, the determining of the fertility prediction is supplemented with quantitative measurement data selected from a group consisting of relaxation parameters, diffusion constants and diffusion tensor mapping, multiple-quantum NMR data, zero-quantum NMR data, susceptibility mapping data and T2* mapping data.

A further aspect of the invention relates to an apparatus for automated noninvasive determining a property of a bird's egg, in particular the fertility or the sex of an embryo thereof comprising: an NMR apparatus, and a conveying device for conveying a plurality of bird eggs sequentially or in parallel into said NMR apparatus and out of said NMR apparatus, wherein said NMR apparatus is configured for subjecting the bird eggs to an NMR measurement, wherein said apparatus further comprises a classification module configured to receive NMR data obtained in said NMR measurement and/or data derived therefrom, said classification module configured for determining, based on said NMR data and/or data derived therefrom, a prediction of the property of the egg, and an egg sorting device for sorting the eggs according to the egg property prediction provided by said classification module.

In a preferred embodiment said NMR apparatus is configured for subjecting the bird eggs to an NMR measurement, such as to generate a 3-D NMR image of at least a part of each of said eggs, said 3-D NMR image having a spatial resolution in at least one dimension of 1.0 mm or less, preferably of 0.50 mm or less, wherein said part of the egg includes the germinal disc of the respective egg (14), and wherein said classification module (38) is configured for determining a prediction of the fertility according to at least one of the following two procedures:

(i) deriving at least one feature from each of said 3-D NMR images, and employing said at least one feature in a feature-based classifier for determining a prediction of the fertility, wherein said at least one feature is chosen from the group consisting of a diameter of the germinal disc, the volume of the germinal disc, the shape of the germinal disc, the texture of the germinal disc, the location of the germinal disc in the egg, the texture of the yolk, a number and/or position of NMR-visible rings in the yolk, a contrast of the rings within of the yolk, a texture, a volume or a shape of the latebra, the length of the neck of the latebra and ratios between the volumes or surfaces of two or more of the yolk, the latebra, the germinal disc and the albumen, and (ii) using a deep learning algorithm, and in particular a deep learning algorithm based on convolutional neural networks, generative adversarial networks, recurrent neural networks or long short-term memory networks.

In procedure (i), preferably at least two features are derived from said 3-D NMR images and employed in said feature-based classifier, wherein at least one of said at least two features is chosen from the group referred to in the preceding paragraph, and wherein preferably, at least one of said at least two features is chosen from the group consisting of the diameter of the germinal disc, the volume of the germinal disc and the shape of the germinal disc, wherein said procedure is preferably a machine learning-based procedure.

In a preferred embodiment, the feature-based classifier employs a kernel method, in particular a support vector machine or a relevance vector machine, a kernel perception, a quadratic discriminant analysis or a linear discriminant analysis, classification trees, random forests or a naïve Bayes classifier. Herein, said classification module is further configured for applying a boosting technique, in particular an adaptive boosting technique, a logistic boosting technique or a probabilistic boosting-tree technique.

In a preferred embodiment, said NMR apparatus is configured to determine, in said NMR measurement, a histogram of diffusion coefficients in various locations in the egg, and wherein the classification module is configured for basing said prediction of the fertility on the shape of the histogram. Herein, determining the fertility is preferably based on the shape of the histogram of diffusion coefficients comprises comparing the frequency of occurrence of at least two different diffusion coefficients or diffusion coefficient ranges, wherein said at least two different diffusion coefficients, or the centers of said at least two diffusion coefficient ranges are preferably separated by between 0.5 and 2.5 mm$^2$/s, more preferably by between 0.75 and 1.5 mm$^2$/s, and/or wherein of said at least two different diffusion coefficients, or of the centers of said at least two diffusion coefficient ranges, one is preferably located in a range of 0.6 to 1.3 mm$^2$/s, more preferably in a range of 0.7 to 1.2 mm$^2$/s, and the other one is preferably located in a range of 1.5 to 2.5 mm$^2$/s, more preferably in a range of 1.7 to 2.3 mm$^2$/s, and/or wherein said various locations in the egg are evenly distributed in the egg, and in particular, correspond to voxels of a diffusion coefficient image.

In a preferred embodiment, said NMR apparatus is configured to determine, in said NMR measurement, an NMR spectrum of the yolk including peaks corresponding to water and fat, and further to predict the fertility based on said NMR spectrum. Herein, said determining a prediction of fertility based on the NMR spectrum preferably comprises determining said prediction of fertility based on the ratio of peaks corresponding to water and fat in said NMR spectrum.

In a preferred embodiment of the apparatus, said eggs are arranged in a regular pattern, in particular in a matrix configuration, on a tray during said conveying and NMR measurement, wherein the number of eggs arranged on said tray is preferably at least 36, more preferably at least 50 and most preferably at least 120.

In a preferred embodiment of the apparatus, said NMR apparatus comprises an array of RF coils for applying RF magnetic fields to the eggs located on the tray and/or for detecting NMR signals, said array of RF coils comprising one or more of a plurality of coils arranged in a plane located above the tray loaded with eggs when conveyed to the NMR apparatus, a plurality of coils (30a) arranged in a plane located underneath the tray loaded with eggs when conveyed to the NMR apparatus, a plurality of coils arranged in vertical planes extending between rows of eggs on the tray when conveyed to the NMR apparatus, which rows extend in parallel with the conveying direction of the tray into and out of the NMR apparatus, wherein in case of the plurality of coils arranged in a plane located above or underneath the tray loaded with eggs, the ratio of the number of coils to the number of eggs arranged on said tra is preferably between 1:1 to 1:25, more preferably between 1:1 to 1:16, and most preferably between 1:1 to 1:5.

In a preferred embodiment, said NMR apparatus comprises an array of RF coils for applying RF magnetic fields to the eggs located on the tray and/or for detecting NMR signals, said array of RF coils being integrated with or attached to said tray, wherein the tray preferably comprises a plurality of dimples or pockets for receiving a corresponding egg, and wherein a number of coils is associated with each of said dimples or pockets, wherein said number of coils per dimple or pocket is at least 1, preferably at least 2, more preferably at least 3 and most preferably at least 4, and/or wherein at least some of said coils are arranged vertically with respect to the main plane of the tray, or with an angle of at least 50°, preferably of at least 75° and most preferably of at least 80° with respect to the main plane of the tray.

In a preferred embodiment, said NMR apparatus is configured for obtaining 3-D NMR images of the plurality of eggs using parallel imaging, in which coherent images from an array of eggs based on measurements with multiple RF coils are reconstructed.

In addition or alternatively, the NMR apparatus is configured for obtaining said 3-D NMR images of the plurality of eggs using a simultaneous multi-slice (SMS) technique, in which multiplexed images from an array of eggs (14) based on measurements at different frequency bands are reconstructed.

In addition or alternatively, said NMR apparatus is configured for generating the 3-D NMR images using compressed sensing, permitting to recover images from measurements sampled below the Nyquist limit.

In addition or alternatively, said NMR apparatus is configured for generating the 3-D NMR images using one or more of steady-state free precession imaging, fast low-angle shot imaging and quantitative transient-state imaging.

In addition or alternatively, said NMR apparatus is configured for improving the quality of the NMR images by means of a quality transfer technique.

In a preferred embodiment of the apparatus, the number of eggs conveyed in parallel to said NMR apparatus and the generation of NMR images is adapted such that the determining of the fertility prediction can be carried out at a rate of 20 seconds per egg or less, preferably of 10 seconds per egg or less, and most preferably of 2 seconds per egg or less.

In a preferred embodiment, said NMR apparatus is configured for generating a 3-D NMR image of a plurality of eggs arranged in a regular pattern, in particular in a matrix configuration, and for dividing the image corresponding to the individual eggs.

In a preferred embodiment, said NMR apparatus is further configured for obtaining quantitative measurement data selected from a group consisting of relaxation parameters, diffusion constants and diffusion tensor mapping, multiple-quantum NMR data, zero-quantum NMR data, susceptibility mapping data and T2* mapping data.

SHORT DESCRIPTION OF THE FIGURES

Figure 3:
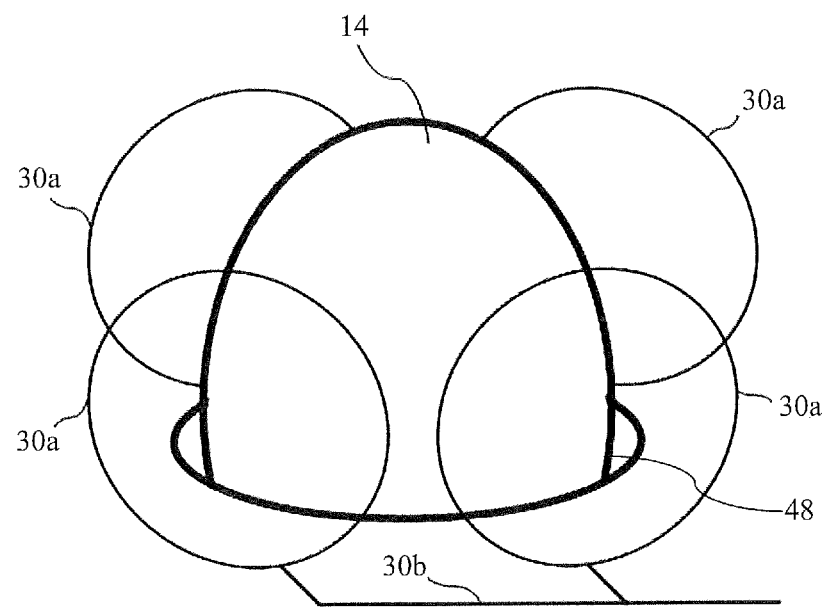

FIG. 3 schematically shows a portion of a tray including a dimple for receiving an egg and four RF coils integrated within the tray surrounding the egg.

Figure 4:
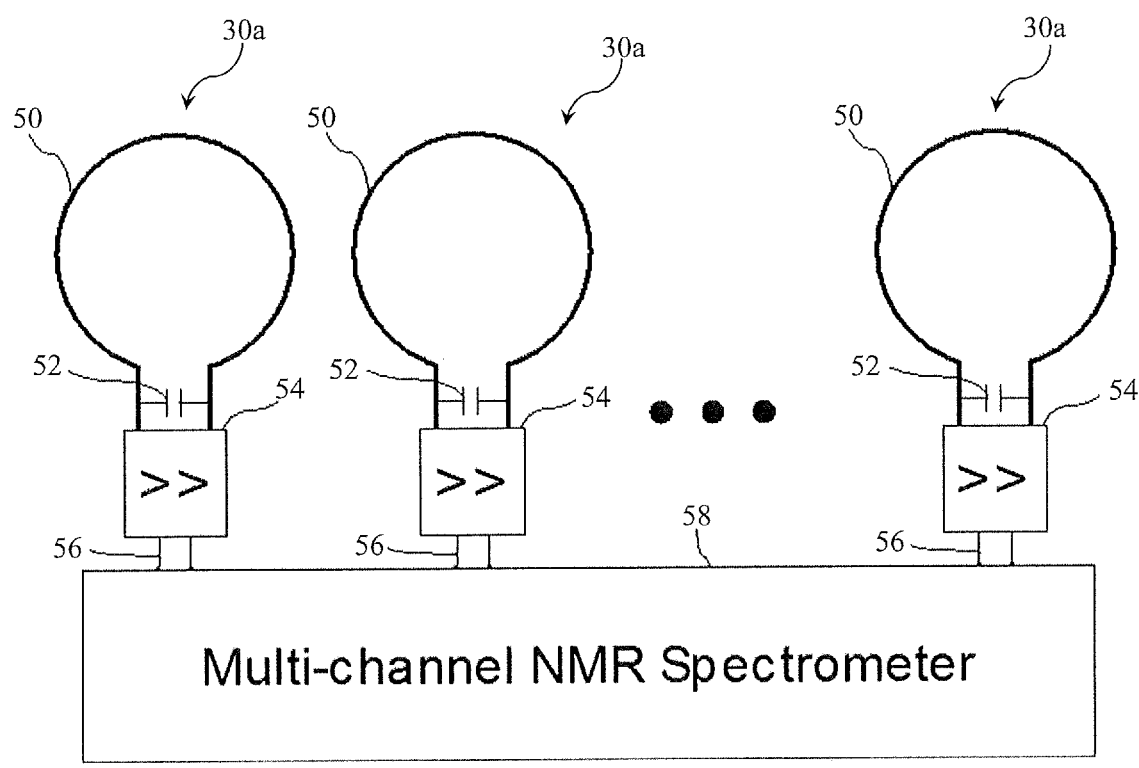

FIG. 4 shows further details of the coil arrays of FIGS. 2A to C and 3.

Figure 5:
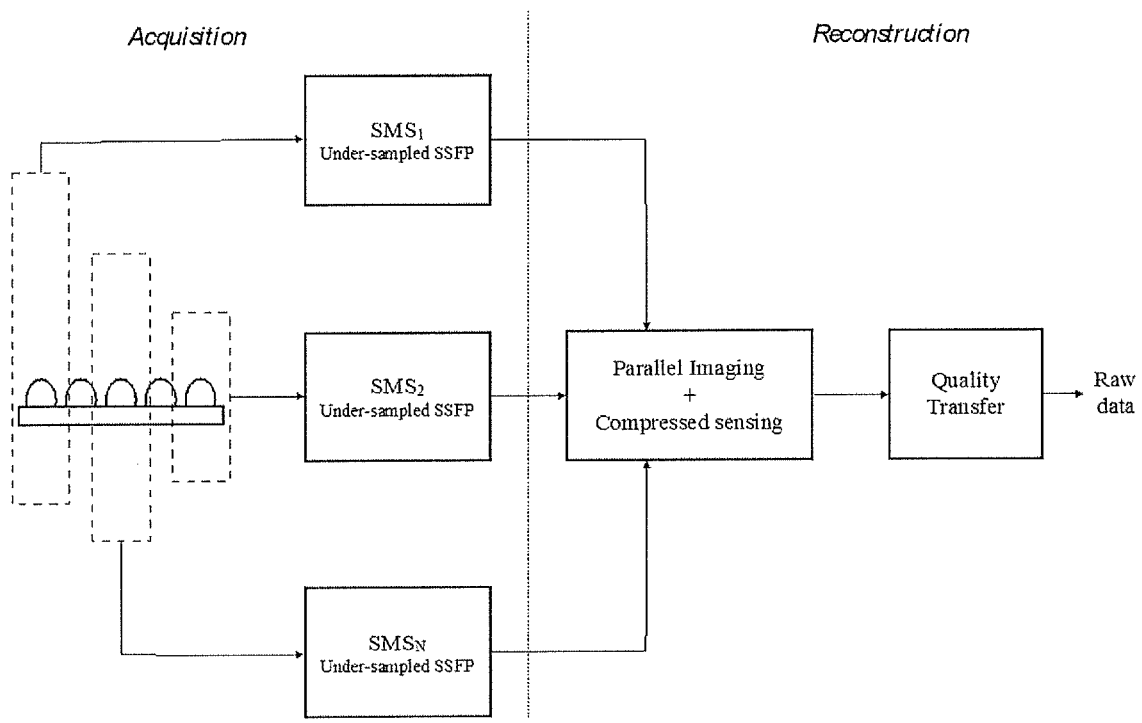

FIG. 5 is a diagram example illustrating an ultra-fast acquisition and reconstruction for NMR imaging.

Figure 6:
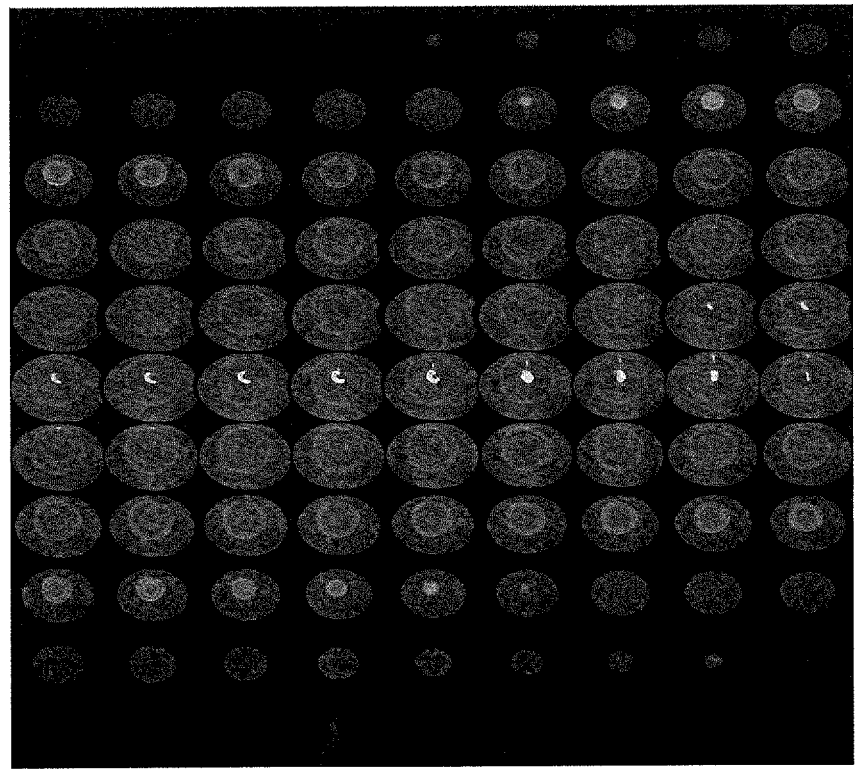

FIG. 6 shows a 3-D volume (represented as a plurality of 2-D slices) of an NMR image that can be input to a machine-learning-based procedure for classification.

Figure 7:
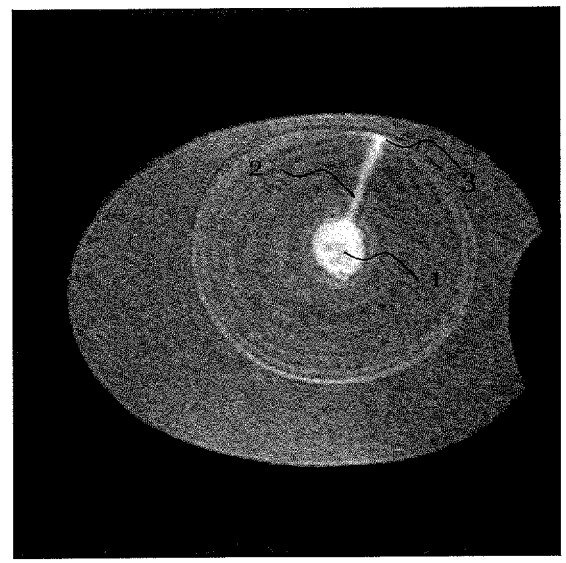

FIG. 7 is an NMR image of an egg showing the latebra, the neck of the latebra and the germinal disc.

Figure 8:
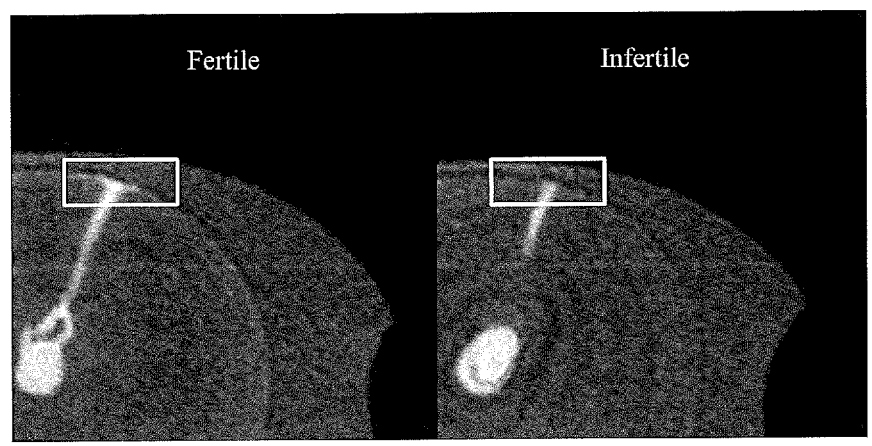

FIG. 8 shows two NMR images including the germinal disc for a fertile egg (left) and an infertile egg (right).

Figure 9:
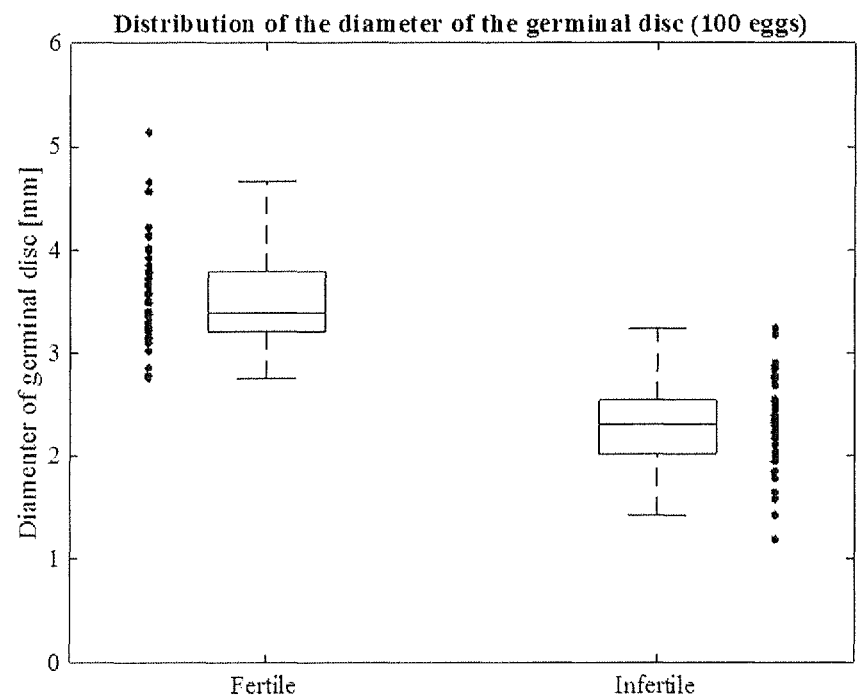

FIG. 9 shows the distribution of the diameter of germinal discs for fertile and infertile eggs.

Figure 10:
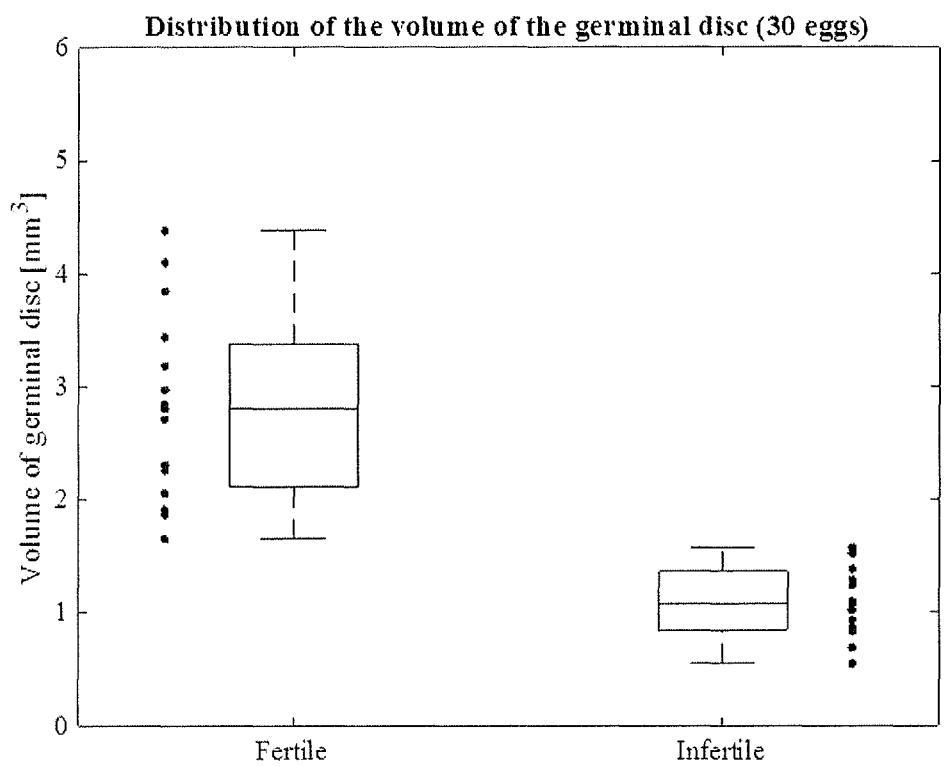

FIG. 10 shows the distribution of the volume of germinal discs for fertile and infertile eggs.

Figure 11:
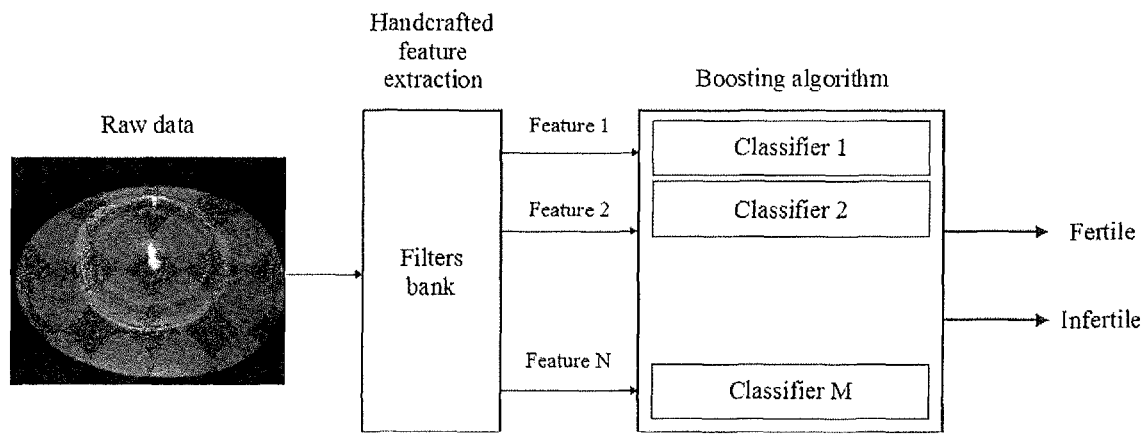

FIG. 11 is a schematic diagram illustrating a machine learning classifier based on handcrafted feature extraction and a boosting algorithm.

Figure 12:
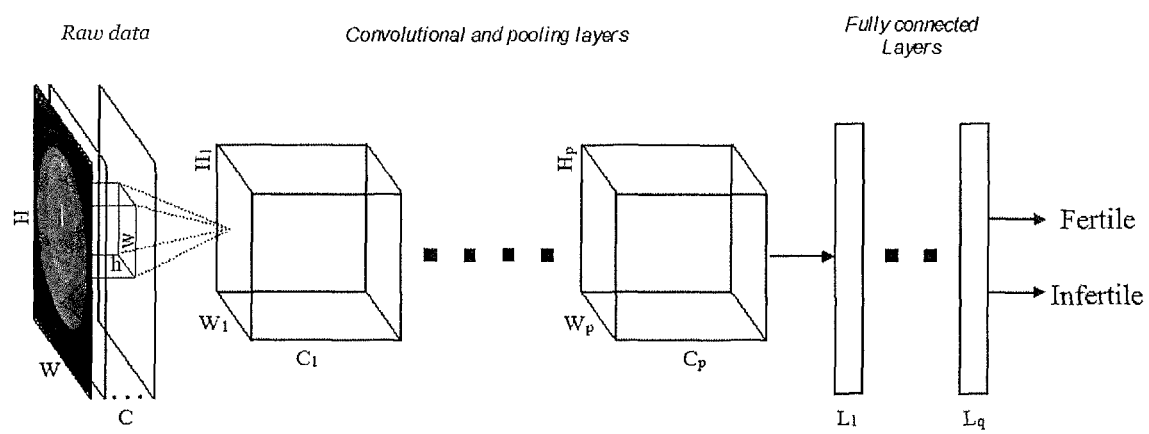

FIG. 12 is a schematic diagram illustrating a convolutional neural network (CNN) architecture used in various embodiments of the present invention.

Figure 13:
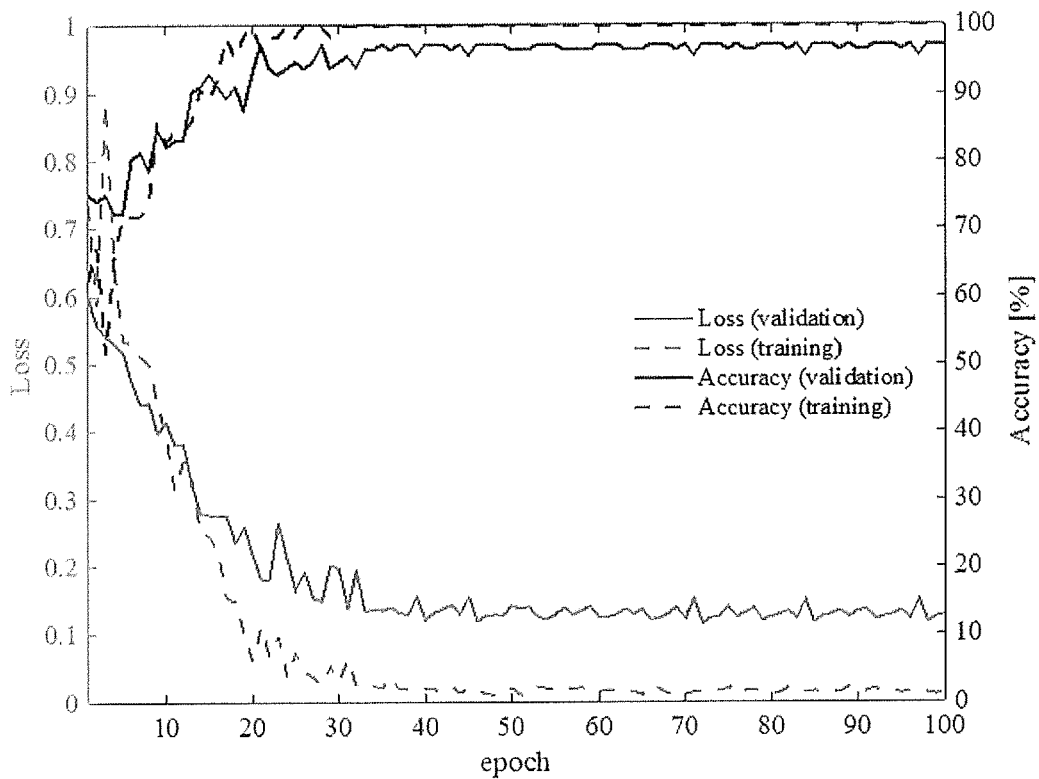

FIG. 13 shows classification results based on the CNN architecture of FIG. 12.

Figure 14:
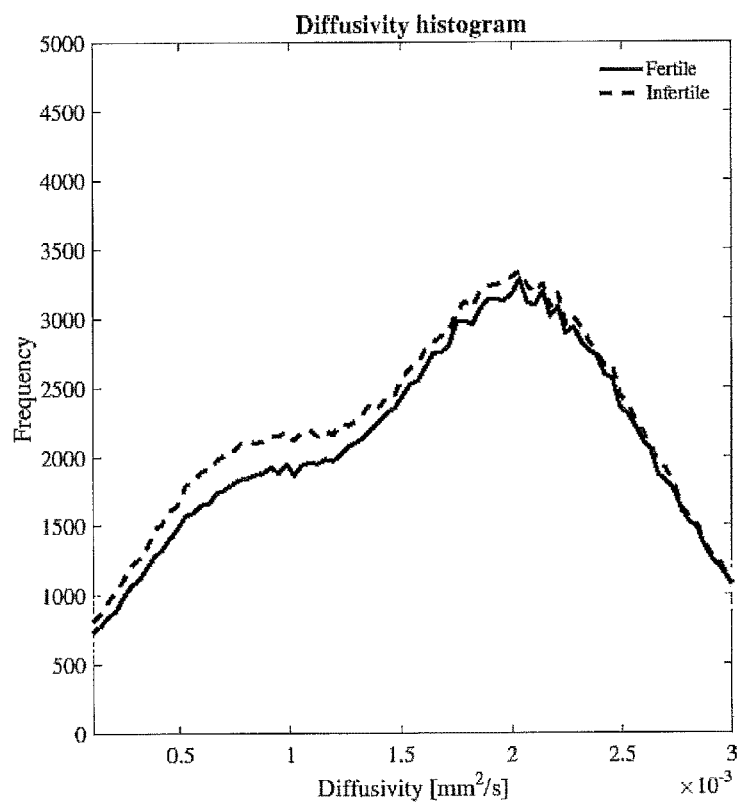

FIG. 14 shows an averaged histogram of the diffusion coefficient observed for a plurality of fertile eggs (solid line) and infertile eggs (broken line).

Figure 15:
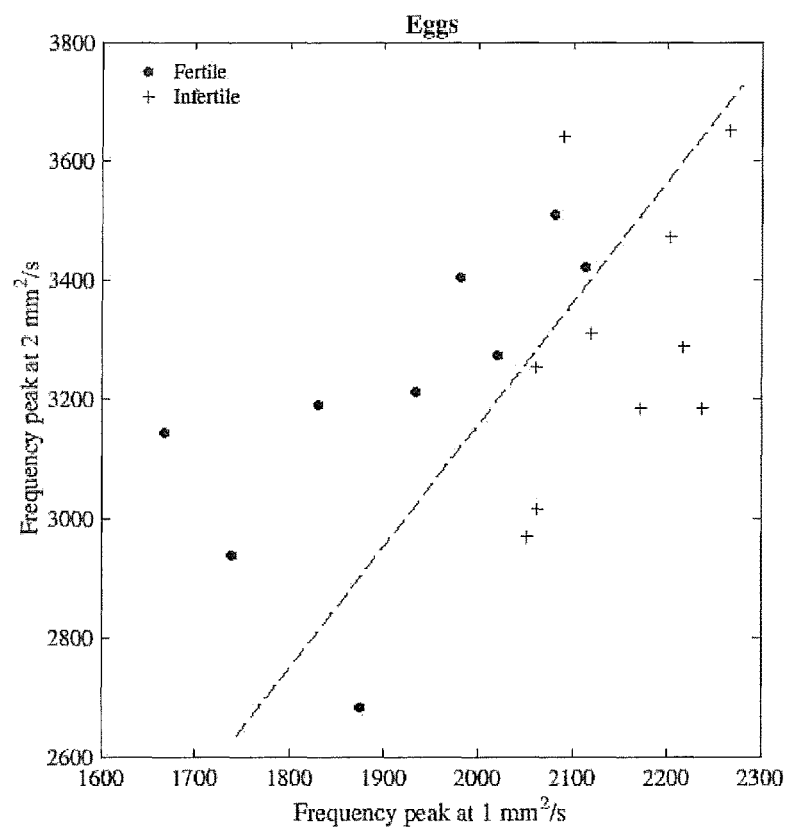

FIG. 15 is a scatterplot showing pairs of diffusion coefficient histogram values at 1 mm$^2$/s and 2 mm$^2$/s for a plurality of eggs.

Figure 16:
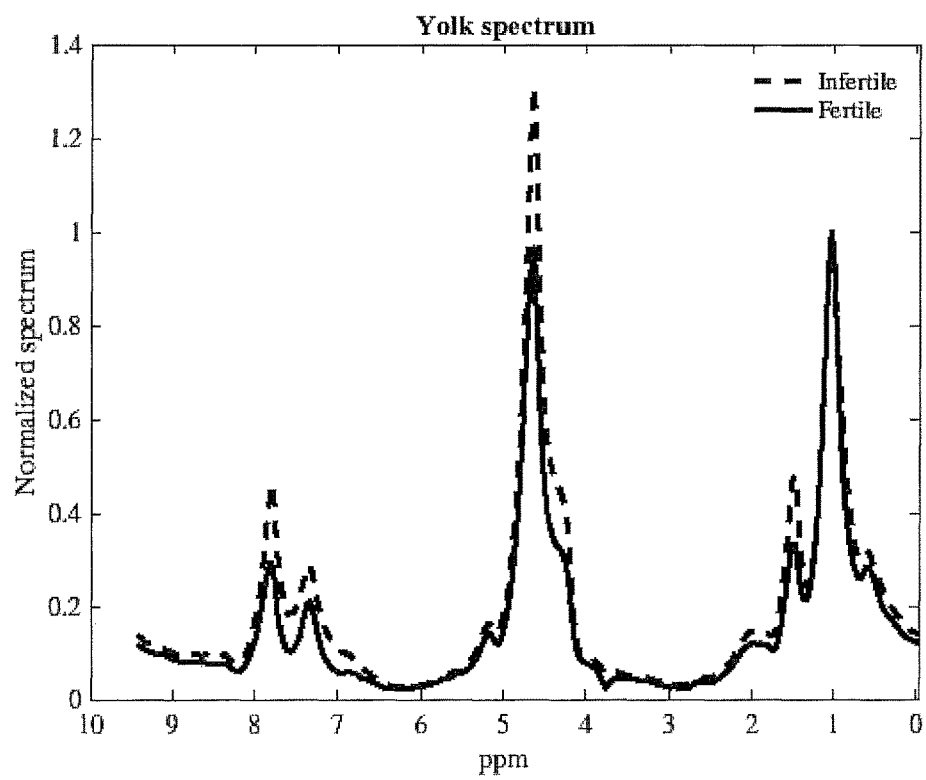

FIG. 16 shows NMR spectra for fertile and infertile eggs.

DESCRIPTION OF THE PREFERRED EMBODIMENT

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to one skilled in the art to which the invention relates.

Figure 1:
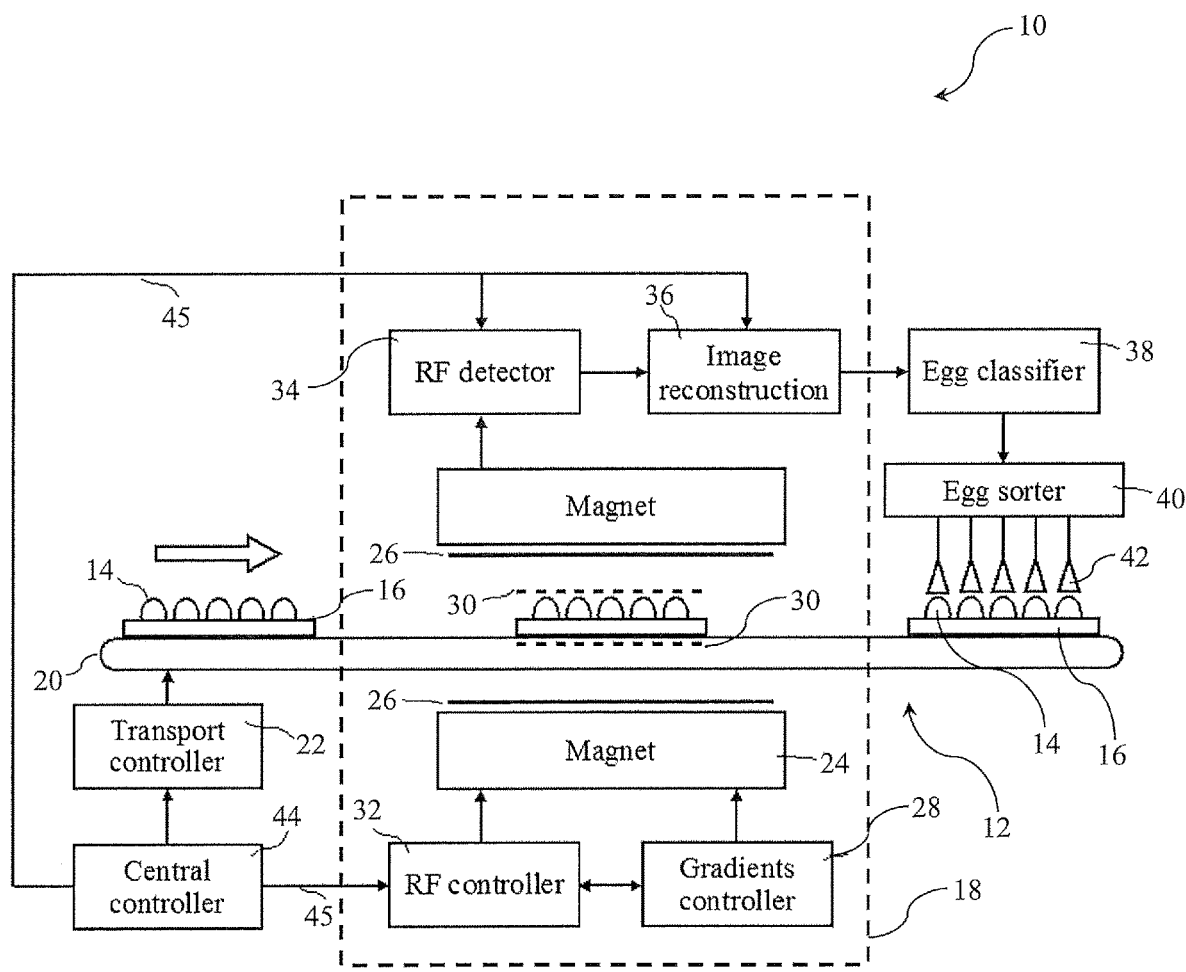
FIG. 1 is a schematic illustration of an apparatus for automated noninvasive determining the fertility of a bird's egg.

FIG. 1 shows a schematic representation of an apparatus 10 according to a preferred embodiment of the invention. The apparatus 10 comprises a conveying device 12 for conveying a plurality of eggs 14 arranged in a matrix configuration on a tray 16 into and out of an NMR apparatus 18, which is represented by the hatched box in the figure. In the embodiment shown, the conveying device 12 comprises a conveyor belt 20 on which the trays 16 may be carried. The movement of the conveyor belt 20 is controlled by a corresponding transport controller 22.

The NMR apparatus 18 comprises a magnet arrangement 24 for providing an external magnetic field in z-direction with which the nuclear spins may interact. The z-direction of the magnetic field coincides with the transport direction on the conveyor belt 20, but this is not crucial for the function of the apparatus 10. In the embodiment shown, the magnet arrangement 22 generates a static magnetic field having a field strength of IT, but the invention is not limited to this. Instead, a wide variety of magnetic field strengths may be used, and in alternative embodiments of the invention, even the earth magnetic field strength could be sufficient, as is demonstrated in Stepišnik, J., Eržen, V. & Kos, M. *NMR imaging in the earth's magnetic field. Magn. Reson. Med.* 15, 386-391(1990), and Robinson, J. N. et al. *Two-dimensional NMR spectroscopy in Earth's magnetic field. J. Magn. Reson.* 182, 343-347(2006).

Further, the NMR apparatus 18 comprises gradient coils 26 which are used to generate spatial gradient fields that are used for image encoding, or in other words, space resolved NMR measurements, in a manner per se known to the skilled person, and further described in Lauterbur, P. C. *Image formation by induced local interactions. Examples employing nuclear magnetic resonance. Nature* 242, 190-191 (1973). In addition, the gradient coils 26 are also used to increase the local homogeneity of the external magnetic field created by the magnet arrangement 24. The gradient fields applied by the gradient coils 26 are controlled by a gradient controller 28. In the embodiment shown, the gradient controller 28 is optimized for an efficient coverage of the measurement space (the k-space), in order to increase the measurement speed. In particular, the gradient controller 28 is preferably configured for carrying out echo-planar-imaging. For details of echo-planar-imaging, reference is made to Stehling, M., Turner, R. & Mansfield, P. *Echo-planar imaging: magnetic resonance imaging in a fraction of a second. Science* (80-.). 254, 43-50 (1991), and Mansfield, P. & Maudsley, A. A. *Planar spin imaging by NMR. J. Phys. C Solid State Phys.* 9, L409-L412 (1976). In an alternative, the gradient controller 28 can control the gradient coils 26 to carry out spiral readouts with time-optimal gradient design, as described in Hargreaves, B. A., Nishimura, D. G. & Conolly, S. M. *Time-optimal multidimensional gradient waveform design for rapid imaging. Magn. Reson. Med.* 51, 81-92 (2004), which allows for very rapid NMR imaging.

Multiple RF coils 30 are arranged such as to surround the tray 16 loaded with eggs 14 on the conveyor belt 20 when the tray 16 is conveyed to the NMR apparatus 18. As the skilled person will appreciate, the RF coils 30 are used for providing RF pulses that excite spins, and in particular, the spins of hydrogen atoms inside the eggs 14. The timing, shape and strength of the pulses are controlled by the RF controller 32. A serial manipulation of the RF pulses and gradients allows for modulation of the measured signal for fast image encoding. In order to allow for high throughput measurements, fast pulse sequences, such as fast-low angle shot imaging or quantitative transient imaging may be deployed, as described in more detail in the the articles Haase, A., Frahm, J., Matthaei, D., Hanicke, W. & Merboldt, K. D. *FLASH imaging. Rapid NMR imaging using low flip-angle pulses. J. Magn. Reson.* 67, 258-266 (1986)) and Gómez, P. A. et al. *Accelerated parameter mapping with compressed sensing: an alternative to MR Fingerprinting. Proc Intl Soc Mag Reson Med* (2017), co-authored by the present inventors and included herein by reference. These fast pulse sequences are designed to be sensitive to different relevant parameters employed in the present invention, in particular T1 and T2 relaxation and diffusion, but also to fat-water content or magnetization transfer.

Moreover, the precession movement of the excited spins in the external magnetic field provided by the magnet arrangement 24 leads to current flux in the RF coils 30 that can be detected by an RF detector 34. The RF detector 34 translates the current flux from the RF coils 30 into an interpretable signal. This includes analog to digital conversion, signal demodulation and amplification.

The NMR apparatus 18 further comprises an image reconstruction module 36. In preferred embodiments, the measurements from different RF coils 30 will be combined using parallel imaging techniques, and an image reconstruction is achieved through the application of fast Fourier transform (FFT) on the acquired measurements. For details of parallel imaging techniques, reference is made to Pruessmann, K. P., Weiger, M., Scheidegger, M. B. & Boesiger, P. *SENSE: sensitivity encoding for fast MRI. Magn. Reson. Med.* 42, 952-962 (1999), and Uecker, M. et al. *ESPIRiT— An eigenvalue approach to autocalibrating parallel MRI: Where SENSE meets GRAPPA. Magn. Reson. Med.* 71, 990-1001 (2014).

When non-Cartesian sampling is employed, the nonuniform FFT as described in Fessler, J. A. and Sutton, B. *Nonuniform Fast Fourier Transforms Using Min-Max Interpolation. IEEE Trans. Signal Process.* 51, 560-574 (2003) may be employed. In the embodiment shown, the image reconstruction module 36 implements advanced reconstruction algorithms, such as low-rank matrix recovery or iterative algorithms. The image reconstruction module 36 is configured to process data of different dimensionality, namely 1D or 2D NMR signals, 2D images, 3D volumes and 4D time series.

The data processed by the image reconstruction module 36 are transmitted to an egg classification module 38. In the embodiment shown, the egg classification module 38 has two purposes, segmentation and classification. In the high throughput device, the egg classification module 38 first segments the incoming images into image portions corresponding to individual eggs 14. Thereafter, the image portion corresponding to each individual egg 14 is classified according to its fertility state in a manner to be described in more detail below.

The result of the egg classification is provided to an egg sorting device 40. In the embodiment shown, the classification result is provided to the egg sorting device 40 in the form of a matrix containing the encoded fertility states of the eggs 14 on a given tray 16. Based on this information, the egg sorting device 40 may sort out eggs 14 determined as infertile or may rearrange the eggs 14 on the tray 16 according to fertility. As schematically shown in FIG. 1, the egg sorter 40 has as many cups 42 as there are eggs 14 on the tray 16, wherein said cups 42 are connected to a vacuum device (not shown). When a cup 42 is moved closely to the corresponding egg 14, the egg 14 will be attracted to and fixed to the cup 42 by vacuum suction, such that it can be safely picked up and gently be put down at a different location.

Finally, a central controller 44 is provided, which is connected for data communication with each of the aforementioned components involved in the NMR measurement, image reconstruction, egg classification and egg sorting process, via corresponding data channels 45.

The NMR apparatus 18 which is devised for egg classification in industrial environment addresses a well-defined scanning geometry. Eggs 14 are introduced into the NMR apparatus 18 arranged in a matrix configuration with M rows and N columns on a corresponding tray 16, where the columns are arranged parallel to the conveying direction on the conveyor belt 20 of FIG. 1. Various embodiments of the invention employ an array 30 of RF coils 30a that is designed to maximize signal-to-noise ratio and to minimize acquisition time, which will be described next with reference to FIGS. 2 to 4. Since the signal amplitude of radiofrequency decays with the square of the distance from the emitting source, the preferred designs aim at placing the RF coils 30a as close as possible to the eggs 14. Moreover, having an array 30 of RF coils 30a creates spatial redundancy in the receiving field that can be exploited to reduce the scan time.

Figure 2A:
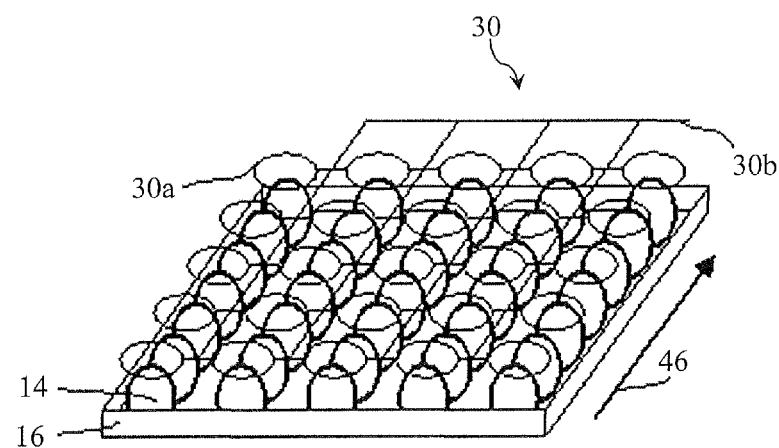
FIG. 2a is a perspective view of an RF coil array arranged in a plane parallel to and slightly above a tray loaded with eggs.
Figure 2B:
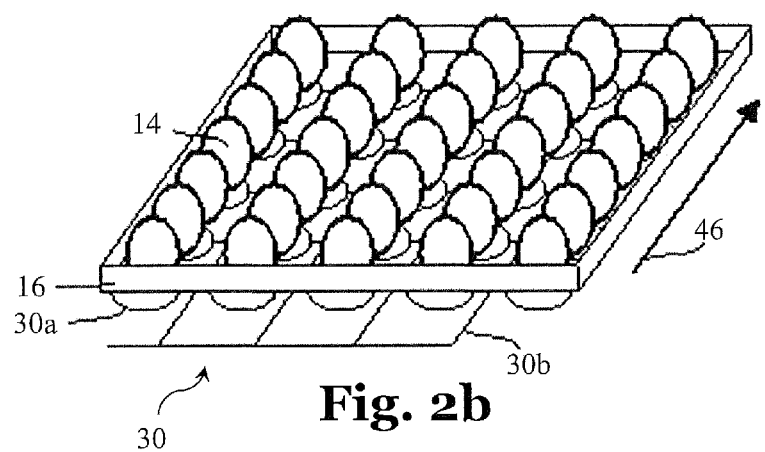
FIG. 2b is a perspective view of an RF coil array arranged in a plane parallel to and slightly below a tray loaded with eggs.
Figure 2C:
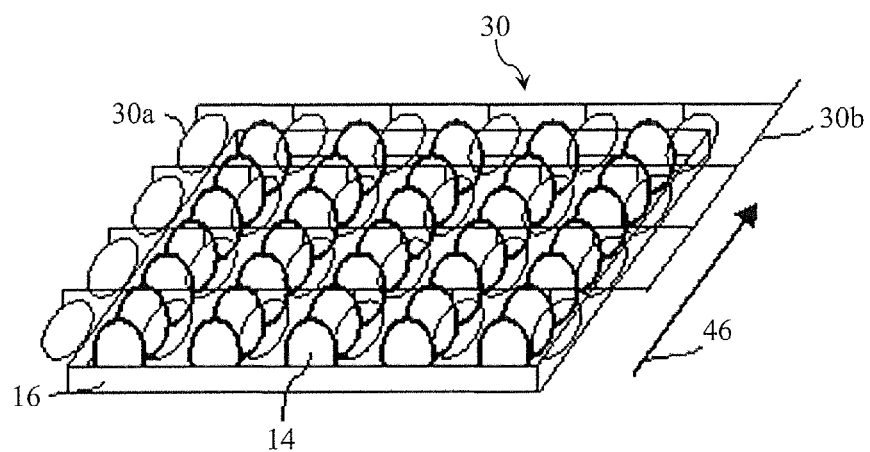
FIG. 2c is a perspective view of an RF coil array in which coils are arranged in vertical planes extending between rows of eggs on the tray, which rows extend in parallel with the conveying direction of the tray.

FIG. 2A to 2C show three different RF coil arrays 30 which are particularly suitable for establishing preferable signal-to-noise ratios and minimum acquisition times. In each of FIGS. 2A to 2C, an array 30 of RF coils 30a is schematically shown together with the tray 16 loaded with eggs 14. Each individual RF coil 30a of the RF coil array 30 is shown to have a loop geometry for simplicity, but different geometries may likewise be implemented. In the embodiment of FIG. 2A, the individual RF coils 30a are arranged in a plane parallel to and slightly above the tray 16. The number of individual RF coils 30a may, but need not correspond to the number of eggs 14. Preferably, the ratio of the number of RF coils 30a to the number of eggs 14 arranged on the tray 16 is between 1:1 to 1:25, more preferably between 1:1 to 1:16, and most preferably between 1:1 to 1:5. Each of the individual RF coils 30a is connected via a corresponding transmission line 30b with the RF controller 32 and with the RF detector 34. While in the simplified figures all of the transmission lines 30b are shown as a single cable, it is to be understood that this cable includes a plurality of individual leads such that each RF coil 30a of the RF coil array 30 can be individually controlled by the RF controller 32 and read out by the RF detector 34. The arrow 46 denotes the direction of the conveying direction of the tray 16 by the conveying device 12.

FIG. 2B shows a similar RF coil array 30 as that of FIG. 2A, which is however placed underneath the tray 16.

FIG. 2C shows an RF coil array 30 of RF coils 30a which are arranged vertically and placed to the side of the eggs 14, rather than above or below, as is the case in FIGS. 2A and 2B. In order not to interfere with the eggs 14 moving on the conveyor belt 20, the RF coils 30a of the RF coil array 30 are arranged in vertical planes extending between the rows of eggs 14 on the tray 16, which rows extend in parallel with the conveying direction of the tray 16 by the conveying device 12 as indicated by the arrow 46.

Since the germinal disc will typically float to the top of the egg 14, the area of interest is mainly located in the upper half thereof. This implies that the configurations of FIG. 2A (superior RF coil array 30 plane) and FIG. 2C (RF coils 30a arranged in longitudinal, vertical planes) allow for smaller distances between the RF coils 30a of the RF coil array 30 and the regions of interest in the eggs 14 than the configuration of FIG. 2B, and hence for a favorable signal-to-noise ratio. However, in various embodiments, the RF coil array 30 arranged in a plane below the tray 16 as shown in FIG. 2B could be used instead of or in combination with any of the configurations of FIGS. 2A and 2C. In fact, any two or all three configurations of FIGS. 2A, 2B and 2C can be combined in the NMR apparatus 18.

In an alternative embodiment, the RF coils 30a are attached to or integrated in the tray 16, as shown in FIG. 3. FIG. 3 schematically shows a portion of the tray 16, in which a dimple 48 for receiving an egg 14 is formed. Attached to or integrated within the tray 16 are four RF coils 30a surrounding the egg 14. Generally, one or more RF coils 30a per dimple 48 may be provided. Other particularly favorable embodiments provide for three, five, six or eight RF coils 30a per dimple 48. Attaching to or integrating the RF coils 30a within the tray 16 allows for a denser integration of RF coils 30a and smaller distances to the corresponding eggs 14, without interfering with the conveying of the eggs 14 on the tray 16, which allows for particularly high signal-to-noise ratios and minimized acquisition time. However, in this embodiment, the eggs 14 need to be transferred from transportation trays (not shown) to specific NMR trays 16, and later on to the incubation trays (not shown).

FIG. 4 shows further details of the RF coil arrays 30, which may apply irrespective of the particular geometrical arrangement of the RF coils 30a in the RF coil array 30, and may hence apply for any of the embodiments shown in FIGS. 2A, 2B, 2C and 3. As is schematically shown in FIG. 4, each of the RF coils 30a may comprise an antenna section 50, which in the shown embodiments has the shape of a circular loop. However, antenna sections 50 with different geometries, such as Helmholtz coils, solenoidal coils, saddle coils or birdcage coils may likewise be employed.

Further, each RF coil 30a comprises a tuning capacitor 52 for reducing the mutual inductance and to tune the center frequency, and a pre-amplifier 54 which improves the tuning, matching and decoupling. Moreover, each RF coil 30a is connected via transmission lines 56 with a multichannel NMR spectrometer 58, which combines the functionalities of the RF controller 32 and the RF detector 34 shown in FIG. 1.

Obviously, the NMR measurement time is critical for a high throughput device. Preferred embodiments of the invention are therefore optimized for high-speed acquisition and reconstruction. In particular, the RF coil arrays 30 described above are suitable for parallel imaging, to thereby acquire less information per RF coil 30a and combining it using spatial redundancy, such as to speed up the measurement.

Preferred embodiments of the invention employ the so-called SENSE method described in Pruessmann, K. P., Weiger, M., Scheidegger, M. B. & Boesiger, P. SENSE: sensitivity encoding for fast MRL Magn. Reson. Med. 42, 952-962 (1999), which makes use of the spatial redundancy to acquire a subsample of the k-space and reconstruct non-aliased images. A related method that is likewise applicable is the so-called Generalized Auto calibrating Partially Parallel Acquisition (GRAPPA) method, as described in Griswold, M. A. et al, *Generalized auto calibrating partially parallel acquisitions (GRAPPA)*, Magn. Res. Med 47, 1202-1210 (2002).

To further increase the throughput, multiband technologies are employed which use several excitation frequencies to allow parallel acquisition at different spatial locations along the bore of the magnet arrangement 24, thereby also reducing the total scan time. A more detailed explanation of the multiband technology is given in Feinberg, D. A. et al. *Multiplexed echo planar imaging for sub-second whole brain fmri and fast diffusion imaging*. PLoS One 5, (2010), which is included herein by reference.

On top of these techniques, in preferred embodiments a so-called compressed sensing is employed, which reduces the number of measuring points necessary to reconstruct an image, thereby introducing a further acceleration factor. A determination of compressed sensing is given in Lustig, M., Donoho, D. & Pauly, J. M. *Sparse MR: The application of compressed sensing for rapid MR imaging*. Magn. Reson. Med. 58, 1182-1195 (2007).

Moreover, in preferred embodiments, the imaging is acquired in the transient state, which can be carried out in an ultrafast manner and use quantitative parameters, as is described in the works co-authored by the present inventors, see Gómez, P. A. et al. *Accelerated parameter mapping with compressed sensing: an alternative to MR Fingerprinting*. Proc Intl Soc Mag Reson Med (2017). Another suitable way of transient imaging is described in Ma, D. et al. *Magnetic resonance fingerprinting*. Nature 495, 187-192 (2013).

The RF coil array configurations and the image reconstruction methods previously introduced allow for quickly imaging the 3D space that contains the N×M array of eggs 14. Depending on the RF coil geometry and on the processing method chosen, in some embodiments one image per egg 14 will be reconstructed, while in other embodiments, a single image per tray 16 will be reconstructed. In the case of a single image per egg 14, each image can be classified individually. In the case of one image per tray 16, the individual eggs 14 in the image need first to be segmented prior to classification. There are multiple segmentation techniques that can be employed; but, given the simplicity of geometry of the trays 16, the preferred solution is to pre-define a grid corresponding to each dimple 48 with a single egg 14.

To achieve a high number of eggs scanned per second, in preferred embodiments a fast pulse sequence is used. These are typically characterized for not being limited by the repetition time (TR). Among them, the preferred one is steady state free precession (SSFP), as is for example described in Carr, H. Y. *Steady-state free precession in nuclear magnetic resonance*. Phys. Rev. 112, 1693-1701 (1958). This family of pulse sequences applies repeated RF excitations to the protons in a very short repetition time (TR), in the order of tens of milliseconds. As a result, the magnetization never fully recovers, but reaches a steady state after several RF excitations. When that happens, one can read a portion of the image in each of these ultra-short TRs, aggregating them to cover the entire measurement space rapidly. This family of sequences is characterized for being highly efficient in terms of signal to noise ratio per unit of time. Along these lines, fast low-angle shot imaging (FLASH) as referred to above might also be used. As SSFP, it has a TR in the order of tens of milliseconds, but contrary to SSFP, it assumes signal recovery after each TR due to the small excitation induced by a low flip angle. Under the same principles, magnetic resonance fingerprinting and quantitative transient-state imaging take the acquisition to the limit measuring in the transient state (before reaching the steady state). They have the advantage of not only producing structural images, but also quantitative maps of the magnetic parameters of the tissue.

To further reduce the acquisition time, one can measure samples below the Nyquist limit and reconstruct using parallel imaging, as disclosed in the works by Pruessmann et al., Griswold, M. A. et al. and also in Uecker, M. et al. *ESPIRiT—An eigenvalue approach to autocalibrating parallel MRI: Where SENSE meets GRAPPA*. Magn. Reson.

Med. 71, 990-1001 (2014)) and compressed sensing as described in the above-references work by Lustig et al. Parallel imaging takes advantage of using coil redundancy and spatial information brought by the coverage of the RF coils. For instance, in an array of RF coils covering a region of the space, each coil will measure different signals given that they are placed at different locations. The differences between these signals, together with the RF sensitivity map of each coil, allows to recover the missing information. This concept can be taken further with compressed sensing. Compressed sensing makes use of redundancy and correlations present in natural images. By taking advantage of these correlations, it is possible to sample below the Nyquist limit and still recover full images. In order to work, compressed sensing requires randomized sampling patterns and non-linear reconstructions that enforce data consistency combined with regularization. The final result of combined parallel imaging and compressed sensing are significantly accelerated acquisitions.

An additional level of parallelization is available with the use of simultaneous multi-slice (SMS), as is described in Feinberg et al. referred to above. This technique multiplexes the acquisition problem in different frequency bands by using multi-band RF pulses. Therefore, it is possible to acquire multiple regions of the scanned object at the same time at multiple frequency bands.

Finally, it is also possible to acquire data at coarser resolutions and reduce the voxel size during reconstruction by a so-called quality transfer step. The quality transfer method is described in further detail in Alexander, D. C. et al. *Image quality transfer and applications in diffusion MN. Neuroimage* 152, 283-298 (2017) and Tanno, R. et al. *Bayesian Image Quality Transfer with CNNs: Exploring Uncertainty in dMRI Super-Resolution.* (2017). These methods rely on a machine learning approach where a model, e. g. a random forest, is trained to capture the high-resolution details and transfer them to low-resolution data.

All NMR imaging techniques generally share a two-step process to scan an image: acquisition and reconstruction. Typically, in MRI, the acquisition time has been much longer than the reconstruction time. The combination of fast pulse sequences with multi-band, parallel imaging and compressed sensing, trades acquisition time for reconstruction time and the latter can greatly benefit from computational power and smart reconstruction algorithms that recover the original image. As a result, the overall time of acquisition and reconstruction is reduced in several orders with this configuration. A schematic illustration summarizing the above is shown in FIG. 5.

Using the apparatus 10 shown in FIG. 1, together with the coil arrays 30 as explained with reference to FIG. 2 to FIG. 4, a 3-D volume of an egg shown as a plurality of 2-D slices of an NMR image of the type shown in FIG. 6 can be generated.

For the purpose of the invention, the most interesting part of the 3-D NMR image is the part including the germinal disc. FIG. 7 shows a slice of a 3-D NMR image, in which the latebra 1, the neck of the latebra 2 and the germinal disc 3 can be discerned.

FIG. 8 shows two NMR image slices for comparison, showing a fertile egg on the left and an infertile egg on the right. In each case, the germinal disc is located in the white square. It is seen that the germinal disc of the fertile egg differs in size and shape from that of the infertile egg.

FIG. 9 shows the distribution of diameters of the germinal disc, as extracted from the NMR image data of 100 different eggs, and sorted according to fertile and infertile state. It is seen that the diameters of the germinal disc in the fertile eggs are larger than those in the infertile eggs. However, there is some overlap, so that a distinction based on the diameter alone would have to face prediction errors in practice.

FIG. 10 shows the distribution of volumes of the germinal disc, as extracted from the NMR image data of 30 different eggs, and sorted according to fertile and infertile state. It is seen that the volume of the germinal disc in the fertile eggs is larger than in the infertile eggs, but a distinction based on the measured volume alone would have to face prediction errors in practice as well.

In order to provide a reliable prediction of the fertility, according to one embodiment of the invention, at least two features are derived from each of the 3-D NMR images, and said at least two features are employed in a feature-based classifier for determining a prediction of the fertility. By basing the classification on at least two features, ambiguities that could arise by relying only on the diameter or the volume of the germinal disc can be significantly decreased, or even removed at all. Promising features to be used for this purpose are the diameter and the volume of the germinal disc, because from the NMR measurements presented herein it is seen that these features are by themselves characteristic for the fertility of the egg. In preferred embodiments, at least one of the features used for classification therefore corresponds to the diameter or the volume of the germinal disc. A further useful feature is the shape of the germinal disc. As can be seen from FIG. 8, in the fertile egg shown on the left, the germinal disc exhibits a "V-shape" in the respective NMR slice, which is in fact found to be characteristic for fertile eggs, and which is missing in the infertile egg on the right of FIG. 8.

However, other features are likewise possible, and accumulating plural features will only improve the accuracy of the classification. For example, features regarding the location of the germinal disc in the egg or the texture of the yolk can be employed. In particular, as is apparent from FIGS. 7 and 8, a plurality of ringlike structures can be seen in the NMR images, which are referred to as "NMR-visible rings" herein. From these "NMR-visible rings", further features can be derived, for example the number of NMR-visible rings, their position in the yolk and/or their contrast within the NMR image. In addition or alternatively, a texture, the volume or shape of the latebra, the length of the neck of the latebra or ratios between the volumes or surfaces of two or more of the yolk, the latebra, the germinal disc and the albumen can be used as features for use in a feature-based classifier for determining a prediction of the fertility. Note that these features are also referred to as "handcrafted features" herein, because these features are predetermined, and the NMR image data is processed such as to derive these specific features therefrom.

For illustration purposes, an example of a machine learning classifier based on handcrafted features is schematically shown in FIG. 11. The classification is composed of two steps. First, the acquired image (raw data) is passed through a bank of filters that are designed to extract N specific features of the image, i.e. volumes, distances, shapes, textures, and more. Based on these features, an N-dimensional classifier is trained. In this example, M weaker classifiers are shown that work together to build a strong classifier using one of the boosting techniques introduced above. These weaker classifiers are for instance SVM, classification tree, perceptron, naïve Bayes classifiers and others.

Instead of relying on predetermined or "handcrafted" features, in other embodiments, feature extraction and classification steps are fully integrated in deep learning architectures like convolutional neural networks (CNN). The idea is, that since it could be demonstrated that the NMR images in principle carry information by which the fertility could be recognized, one can rely on the deep learning architecture to find out the features to be considered in the classification by itself. There are three main elements in these architectures, although depending on the implementation there might be variations:

1. Convolutional layers: Convolutions play a role as image feature extractors. In these layers, the neurons are distributed into feature maps, and are connected to a neighborhood in the previous layers through a set of weights. These weights are different for different feature maps, allowing for several features to be extracted from the same location of the image.
2. Pooling layers: Their aim is to reach spatial invariance to input distortions and translations. They achieve this by reducing spatial resolution and propagating to the next layer some local metric of the feature maps. Several pooling schemes exist, where average and maximum pooling are the most used ones.
3. Fully connected layers: They collect the features extracted by the convolutional and pooling layers and yield a classification based on them.

CNNs need to learn their free parameters (weights and biases) to serve their mission. This process may be based on a loss function that computes the classification error and a training algorithm (e. g. backpropagation) to determine the adjustment of the CNN parameters based on the error. A major challenge of CNNs is to avoid overfitting or the capability to generalize the classification to unseen data. A useful approach to control overfitting is the use of a validation dataset during training, which is employed in favorable embodiments of the present invention. This involves dividing the dataset in two groups, training and validation. As their names indicate, the first is used for training, while the second controls that the accuracy and error improves not only in the training dataset but also in the yet unseen data.

An example of a CNN for use in favorable embodiments of the invention is schematically shown in FIG. 12. The NMR-image with H×W dimensions is convolved with C kernels of size h×w to extract feature maps. Then $C_n$ pooling and convolution operations transform the feature maps dimensions to $H_n \times W_n$, n=[1, p]. Finally, q fully connected layers with $L_m$ neurons per layer (m=[1, q]) take the features derived in the previous steps to yield a classification of the image.

Using a CNN of the general structure shown in FIG. 12 and carrying out a training and validation based on 300 eggs, half of them fertile and half of them infertile, an accuracy of 97.3% in the validation data set could be achieved, as is seen from FIG. 13. Herein, an implementation of the CNN AlexNet (Krizhevsky, A., Sutskever, I. & Hinton, G. E. *ImageNet Classification with Deep Convolutional Neural Networks. Adv. Neural Inf. Process. Syst.* 1-9 (2012). has been employed.

FIG. 13 shows the loss and the accuracy both for training data (i.e. NMR images of 250 eggs) and validation data (NMR data of 50 eggs). It is seen that after 50 training epochs (iterations) the accuracy of the classification with regard to the training data already reaches nearly 100%. This very high rate is due to the aforementioned "overfitting", but the important question is, of course, how the CNN performs on NMR-images of eggs it has not seen during training. This is represented by the accuracy of the validation data, which after 50 training epochs still leads to an accuracy of 97.3%, which demonstrates that the method of the invention clearly works with a reliability and precision that allows for a commercially attractive implementation.

Note that both, the classification based on the feature-based classifier and the deep learning algorithm is fundamentally different from a mere "comparison with NMR images stored in a database", as is suggested in the aforementioned EP 0 890 838 B1. In fact, it is doubted that by such a comparison a reliable fertility prediction can actually be made, and this document does not show any experimental data suggesting this.

In various embodiments of the invention, generative adversarial networks may be employed.

In various embodiments of the invention, generative adversaria] networks may be employed. In generative adversarial networks (GAN), two neural networks are trained at the same time. The first one learns how to generate artificial images from a space of samples and the second one tries to determine if the generated images are artificial or not. They are called adversarial because the generative networks try to "cheat" the classification network by learning how to create images that seem real. There are two ideas behind this: 1) One can eventually move from supervised learning to unsupervised learning creating one's own synthetic dataset and reducing the demand of "real training" images. 2) One can replicate the same architecture to teach a network to generate "fertile and infertile images" and a second one to classify them in an adversarial configuration. For further details, reference is made to Goodfellow, I. J. et al. *Generative Adversarial Networks.* (2014).

FIG. 14 shows an averaged histogram of the diffusion coefficient D observed throughout a plurality of fertile eggs (solid line) and infertile eggs (broken line). In the histogram, for each of the respective parameter bins, the number of voxels falling within the bin is counted. D is the molecular self diffusion coefficient (also referred to as "diffusion constant") of water molecules which was defined by A. Einstein in 1905 (A. Einstein in "Ann Physik", 17, p 549 (1905)). Unlike Fick's law, no "gradient" is needed for its definition. Instead, one may think of a certain small volume of water molecules within a large volume. After waiting a certain time interval t, a number of water molecules will "diffuse" outside of this volume due to Brownian Motion. The diffusion coefficient describes how fast this process is. The equation from Einstein describes the distance X for the water molecules travelling by Brownian Motion:

$$X^2 = 2 \cdot D \cdot t.$$

In NMR, this process can be measured using the water NMR Signal and applying a magnetic field gradient. The diffusion coefficient D of water is changed by several anatomical details. For example, if there is a diffusion barrier, like a cell membrane, D will be decreased.

The diffusion coefficients represented in FIG. 14 have been determined for each of the voxels of a diffusion coefficient image of the entire volume of a plurality of eggs. As is seen from FIG. 14, the histogram has very similar values around 2 mm$^2$/s (corresponding to the albumen), but diffusion coefficients around 1 mm$^2$/s (found in regions within the yolk) are more frequently found in infertile eggs than in fertile eggs. Accordingly, this difference can be taken as a further criterion to determine the fertility, that can be incorporated into the machine learning procedures to thereby further increase the accuracy.

FIG. 15 shows a scatterplot of pairs of diffusion coefficient histogram values at 1 mm$^2$/s and 2 mm$^2$/s, for nine fertile eggs and ten infertile eggs. As can be seen from FIG.

15, in the simple scatterplot, all but one egg of each species is located on a corresponding side of a dashed separation line, which denotes a ratio of the histogram values at 2 mm²/s and 1 mm²/s, which ratio is generally exceeded for fertile eggs and not reached for infertile eggs.

FIG. 16 shows an NMR spectrum of the yolk for fertile and infertile eggs. The spectrum shows a peak at about 1 ppm corresponding to fat and a peek at about 4.7 ppm corresponding to water. The inventors have found that the ratio of the height of the fat peak to the height of the water peak is higher for infertile eggs than for fertile eggs. Accordingly, based on this ratio, the distinction between fertile and infertile eggs can likewise be made.

In preferred embodiments, one or both of the two indicators for fertility, i.e. the shape of the diffusion coefficient histogram and the ratio of the fat and water peaks, can be combined to increase the reliability of the prediction. Note that the comparison of the histogram values at 1 mm²/s and 2 mm²/s is only one way of exploiting the characteristic shape of the diffusion coefficient histogram. In preferred embodiments, the entire diffusion coefficient histogram may be presented to a machine learning algorithm, which automatically learns to distinguish between diffusion coefficient histograms corresponding to fertile and infertile eggs. FIG. 15 indicates that there is enough fertility related information in the diffusivity histogram to make the correct distinction, which can then be properly accounted for by a machine learning module, such as a suitably configured egg classification module 38.

Similarly, while the ratio of the fat and water peaks in the spectrum of FIG. 16 is only one way to distinguish the fertility of the egg based on the spectrum, in alternative embodiments, the entire spectrum could be presented to a machine learning module, such as a suitably configured egg classification module 38, which after sufficient training could distinguish between fertile and infertile eggs based on the spectrum.

LIST OF REFERENCES 1 latebra
2 neck of latebra
3 germinal disc
10 apparatus for noninvasive determining the fertility of an egg
12 conveying device
14 egg
16 tray
18 NMR apparatus
20 conveyor belt
22 transport controller
24 magnet arrangement
26 gradient coils
28 gradient controller
30 RF coil array
30a RF coil
32 RF controller
34 RF detector
36 image reconstruction module
38 egg classification module
40 egg sorting device
42 suction cup of egg sorting device 40
44 central controller
45 data channel
46 transport direction
48 dimple in tray 16
50 antenna section
52 tuning capacitor
54 preamplifier
56 transmission lines
58 NMR spectrometer
60 user interface

The invention claimed is:

1. A method of automated noninvasive determining a fertility of a bird's egg, comprising the following steps:
conveying a plurality of bird eggs sequentially or in parallel into an NMR apparatus,
subjecting the bird eggs to an NMR measurement and generating a 3-D NMR image of at least a part of each of said eggs, said 3-D NMR image having a spatial resolution in at least one dimension of 1.0 mm or less, wherein said part of the egg includes a germinal disc of the respective egg, and
determining a prediction of the fertility by deriving at least one feature from each of said 3-D NMR images, and employing said at least one feature in a feature-based classifier for determining a prediction of the fertility,
wherein said at least one feature is chosen from a group consisting of a diameter of the germinal disc, a volume of the germinal disc, a shape of the germinal disc, a texture of the germinal disc, a location of the germinal disc in the egg, and a ratio between volumes or surfaces of the germinal disc and one of a yolk, a latebra, and an albumen.

2. The method of claim 1, wherein said step of determining the prediction of the fertility is carried out by a classification module, wherein said method further comprises a step of conveying said plurality of bird eggs out of said NMR apparatus and sorting the eggs according to the fertility prediction provided by said classification module.

3. The method of claim 1, wherein the feature-based classifier employs one of a support vector machine, relevance vector machine, a kernel perception, a quadratic discriminant analysis, a linear discriminant analysis, classification trees, random forests, and a naïve Bayes classifier.

4. The method of claim 3, wherein said method comprises applying one of an adaptive boosting technique, a logistic boosting technique and a probabilistic boosting-tree technique.

5. The method of claim 1, wherein said eggs are arranged in a regular pattern on a tray during said conveying and NMR measurement,
wherein a number of eggs arranged on said tray is at least 36.

6. The method of claim 5, wherein said NMR apparatus comprises an array of RF coils for one or both of applying RF magnetic fields to the eggs located on the tray and detecting NMR signals, said array of RF coils comprising one or more of
a plurality of coils arranged in a plane located above the tray loaded with eggs when conveyed to the NMR apparatus,
a plurality of coils arranged in a plane located underneath the tray loaded with eggs when conveyed to the NMR apparatus,
a plurality of coils arranged in vertical planes extending between rows of eggs on the tray when conveyed to the NMR apparatus, which rows extend in parallel with a conveying direction of the tray into and out of the NMR apparatus.

7. The method of claim 5, wherein said NMR apparatus comprises an array of RF coils for one or both of applying RF magnetic fields to the eggs located on the tray and detecting NMR signals, said array of RF coils being integrated with or attached to said tray.

8. The method of claim 1, wherein said 3-D NMR images of the plurality of eggs are obtained using parallel imaging, in which coherent images from an array of eggs based on measurements with multiple RF coils are reconstructed.

9. The method of claim 1, wherein the 3-D NMR images are generated using compressed sensing, permitting to recover images from measurements sampled below the Nyquist limit.

10. The method of claim 1, wherein the 3-D NMR images are generated using one or more of steady-state free precession, fast low-angle shot imaging, and quantitative transient-state imaging.

11. The method of claim 1, further comprising a step of improving the quality of the 3-D NMR images by means of a quality transfer technique.

12. The method of claim 1, wherein the number of eggs conveyed in parallel to said NMR apparatus and the generation of NMR images is adapted such that the determining of the fertility prediction is carried out at a rate of 10 seconds per egg or less.

13. The method of claim 1, wherein a combined 3-D NMR image of a plurality of eggs arranged in a matrix configuration is generated, and the combined 3-D NMR image is divided into a plurality of 3D-NMR images corresponding to the individual eggs, which are subjected to said fertility prediction determining.

14. The method of claim 1, wherein the determining of the fertility prediction is supplemented with quantitative measurement data selected from a group consisting of relaxation parameters, diffusion constants and diffusion tensor mapping, multiple-quantum NMR data, zero-quantum NMR data, susceptibility mapping data and T2* mapping data.

15. An apparatus for automated noninvasive determining a fertility of a bird's egg, said apparatus comprising:
an NMR apparatus,
a conveying device for conveying a plurality of bird eggs sequentially or in parallel into said NMR apparatus and out of said NMR apparatus,
wherein said NMR apparatus is configured for subjecting the bird eggs to an NMR measurement,
wherein said apparatus further comprises a classification module and
an egg sorting device for sorting the eggs according to an egg fertility prediction provided by said classification module, wherein said NMR apparatus is configured for generating a 3-D NMR image of at least a part of each of said eggs, said 3-D NMR image having a spatial resolution in at least one dimension of 1.0 mm or less, wherein said part of the egg includes a germinal disc of the respective egg,
and wherein said classification module is configured for determining a prediction of the fertility by deriving at least one feature from each of said 3-D NMR images, and employing said at least one feature in a feature-based classifier for determining a prediction of the fertility, wherein said at least one feature is chosen from a group consisting of a diameter of the germinal disc, a volume of the germinal disc, a shape of the germinal disc, a texture of the germinal disc, a location of the germinal disc in the egg, and a ratio between volumes or surfaces of the germinal disc and one of a yolk, a latebra, and an albumen.

16. The apparatus of claim 15, wherein at least two features are derived from said 3-D NMR images and employed in said feature-based classifier, wherein at least one of said at least two features is chosen from the group referred to in claim 15, and wherein at least one of said at least two features is chosen from a group consisting of the diameter of the germinal disc, the volume of the germinal disc and the shape of the germinal disc, wherein said procedure is preferably a machine learning-based procedure.

17. The apparatus of claim 15, wherein said eggs are arranged in a regular pattern on a tray during said conveying and NMR measurement,
wherein a number of eggs arranged on said tray is at least 36.

18. The apparatus of claim 17, wherein said NMR apparatus comprises an array of RF coils for one or both of applying RF magnetic fields to the eggs located on the tray and detecting NMR signals, said array of RF coils comprising one or more of
a plurality of coils arranged in a plane located above the tray loaded with eggs when conveyed to the NMR apparatus,
a plurality of coils arranged in a plane located underneath the tray loaded with eggs when conveyed to the NMR apparatus,
a plurality of coils arranged in vertical planes extending between rows of eggs on the tray when conveyed to the NMR apparatus, which rows extend in parallel with a conveying direction of the tray into and out of the NMR apparatus.

19. The apparatus of claim 17, wherein said NMR apparatus comprises an array of RF coils for one or both of applying RF magnetic fields to the eggs located on the tray and detecting NMR signals, said array of RF coils being integrated with or attached to said tray,
wherein the tray comprises a plurality of dimples or pockets for receiving a corresponding egg, and wherein a number of coils is associated with each of said dimples or pockets, wherein said number of coils per dimple or pocket is at least 1.

20. The method of claim 1, wherein at least two features are derived from said 3-D NMR images and employed in said feature-based classifier, wherein at least one of said at least two features is chosen from a group consisting of the diameter of the germinal disc, the volume of the germinal disc and the shape of the germinal disc, wherein said procedure is a machine learning-based procedure.

* * * * *

UNITED STATES PATENT AND TRADEMARK OFFICE
CERTIFICATE OF CORRECTION

PATENT NO. : 11,116,184 B2
APPLICATION NO. : 16/760735
DATED : September 14, 2021
INVENTOR(S) : Gómez et al.

Page 1 of 1

It is certified that error appears in the above-identified patent and that said Letters Patent is hereby corrected as shown below:

In the Claims

In Column 22, Lines 35-36:
Insert --a-- before "relevance vector machine"

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*